US007879062B2

(12) United States Patent  (10) Patent No.: US 7,879,062 B2
Galdonik et al.  (45) Date of Patent: *Feb. 1, 2011

(54) FIBER BASED EMBOLISM PROTECTION DEVICE

(75) Inventors: Jason A. Galdonik, Hanover, MN (US); Matthew F. Ogle, Oronoco, MN (US); Jim Pokorney, Northfield, MN (US); Thomas F. Hinnenkamp, White Bear Lake, MN (US)

(73) Assignee: Lumen Biomedical, Inc., Maple Grove, MN (US)

( * ) Notice: Subject to any disclaimer, the term of this patent is extended or adjusted under 35 U.S.C. 154(b) by 1076 days.

This patent is subject to a terminal disclaimer.

(21) Appl. No.: 10/795,131

(22) Filed: Mar. 6, 2004

(65) Prior Publication Data

US 2005/0085847 A1  Apr. 21, 2005

Related U.S. Application Data

(60) Provisional application No. 60/489,044, filed on Jul. 22, 2003.

(51) Int. Cl.
*A61M 29/00* (2006.01)
(52) U.S. Cl. .................................... 606/200
(58) Field of Classification Search .......... 606/200, 606/108, 113, 114, 127, 159, 191–199; 604/104–107
See application file for complete search history.

(56) References Cited

U.S. PATENT DOCUMENTS 4,422,939 A   12/1983  Sharp et al.
4,512,338 A   4/1985   Balko et al.

(Continued)

FOREIGN PATENT DOCUMENTS

EP   0117940 A2   12/1984

(Continued)

OTHER PUBLICATIONS

4DG? Fibers; http://web.archive.org/web/2011030070010/http://fitfibers.com/4DG_Fibers.htm; (Oct. 30, 2001).*

(Continued)

*Primary Examiner*—Anhtuan T Nguyen
*Assistant Examiner*—Elizabeth Houston
(74) *Attorney, Agent, or Firm*—Dardi & Herbert, PLLC; Peter S. Dardi; Mengmeng Fahrni

(57) ABSTRACT

Improved embolism protection devices comprises fibers that can have one configuration for delivery of the device and a second configuration in which the device is deployed for filtering of flow within a vessel. In some embodiments, the fibers can be connected to a fiber support, which is connected to an actuating element. The actuating element controls the transition from the delivery configuration to the deployed configuration. The embolism protection device can comprise a guidewire. The fibers can be attached at one end to a fiber support structure and at another end to the guidewire. A hypotube can be attached to the proximal end of the fibers while the guidewire is attached at the distal end of the fibers with the guidewire extending within a central channel of the hypotube. The hypotube can be used to guide the delivery of treatment structures, such as a balloon and/or a stent.

47 Claims, 21 Drawing Sheets

U.S. PATENT DOCUMENTS

| | | |
|---|---|---|
| 4,550,126 A | 10/1985 | Lorenz |
| 4,793,348 A | 12/1988 | Palmaz |
| 4,817,600 A | 4/1989 | Herms et al. |
| 4,832,055 A | 5/1989 | Palestrant |
| 5,059,205 A | 10/1991 | El-Nounou et al. |
| 5,200,248 A | 4/1993 | Thompson et al. |
| 5,350,398 A | 9/1994 | Pavcnik et al. |
| 5,370,657 A | 12/1994 | Irie |
| 5,407,673 A | 4/1995 | Reich et al. |
| 5,540,707 A * | 7/1996 | Ressemann et al. ......... 606/159 |
| 5,569,463 A | 10/1996 | Helmus et al. |
| 5,651,765 A | 7/1997 | Haworth et al. |
| 5,704,910 A | 1/1998 | Humes |
| 5,720,764 A | 2/1998 | Naderlinger |
| 5,782,791 A | 7/1998 | Peterson et al. |
| 5,807,306 A | 9/1998 | Shapland et al. |
| 5,810,874 A | 9/1998 | Lefebvre |
| 5,836,868 A * | 11/1998 | Ressemann et al. ......... 606/159 |
| 5,836,962 A * | 11/1998 | Gianotti ...................... 623/1.51 |
| 5,911,704 A | 6/1999 | Humes |
| 5,914,125 A | 6/1999 | Andrews et al. |
| 5,919,145 A | 7/1999 | Sahatjian |
| 5,928,260 A * | 7/1999 | Chin et al. ................... 606/200 |
| 5,935,139 A | 8/1999 | Bates |
| 5,938,645 A | 8/1999 | Gordon |
| 5,941,869 A * | 8/1999 | Patterson et al. ............. 604/508 |
| 5,972,019 A * | 10/1999 | Engelson et al. ............. 606/200 |
| 5,977,429 A | 11/1999 | Phillips et al. |
| 6,066,149 A * | 5/2000 | Samson et al. ............... 606/159 |
| 6,099,864 A | 8/2000 | Morrison et al. |
| 6,103,376 A | 8/2000 | Phillips et al. |
| 6,123,681 A | 9/2000 | Brown, III |
| 6,146,396 A * | 11/2000 | Konya et al. ................. 606/159 |
| 6,160,084 A | 12/2000 | Langer et al. |
| 6,231,589 B1 | 5/2001 | Wessman et al. |
| 6,238,412 B1 | 5/2001 | Dubrul et al. |
| 6,245,088 B1 | 6/2001 | Lowery |
| 6,245,089 B1 | 6/2001 | Daniel et al. |
| 6,254,563 B1 | 7/2001 | Macoviak et al. |
| 6,267,776 B1 | 7/2001 | O'Connell |
| 6,273,901 B1 | 8/2001 | Whitcher et al. |
| 6,306,163 B1 | 10/2001 | Fitz |
| 6,346,116 B1 | 2/2002 | Brooks et al. |
| 6,364,895 B1 * | 4/2002 | Greenhalgh ................. 606/200 |
| 6,364,896 B1 | 4/2002 | Addis |
| 6,368,338 B1 * | 4/2002 | Konya et al. ................. 606/200 |
| 6,368,344 B1 * | 4/2002 | Fitz ........................... 623/1.11 |
| 6,371,969 B1 | 4/2002 | Tsugita et al. |
| 6,371,970 B1 | 4/2002 | Khosravi et al. |
| 6,391,044 B1 | 5/2002 | Yadav et al. |
| 6,391,300 B1 | 5/2002 | Rose et al. |
| 6,450,989 B2 | 9/2002 | Dubrul et al. |
| 6,458,119 B1 | 10/2002 | Berenstein et al. |
| 6,485,501 B1 | 11/2002 | Green |
| 6,485,502 B2 | 11/2002 | Don Michael et al. |
| 6,491,965 B1 | 12/2002 | Berry et al. |
| 6,514,273 B1 | 2/2003 | Voss et al. |
| 6,527,746 B1 | 3/2003 | Oslund et al. |
| 6,558,377 B2 * | 5/2003 | Lee et al. ...................... 606/32 |
| 6,558,405 B1 | 5/2003 | McInnes |
| 6,602,271 B2 | 8/2003 | Adams et al. |
| 6,605,111 B2 | 8/2003 | Bose et al. |
| 6,610,077 B1 | 8/2003 | Hancock et al. |
| 6,645,223 B2 | 11/2003 | Boyle et al. |
| 6,652,505 B1 | 11/2003 | Tsugita et al. |
| 6,676,682 B1 | 1/2004 | Tsugita et al. |
| 6,878,153 B2 * | 4/2005 | Linder et al. ................ 606/200 |
| 6,911,036 B2 | 6/2005 | Douk et al. |
| 7,052,500 B2 | 5/2006 | Bashiri et al. |
| 2002/0062133 A1 | 5/2002 | Gilson et al. |
| 2002/0072550 A1 | 6/2002 | Brady et al. |
| 2002/0111648 A1 | 8/2002 | Kusleika et al. |
| 2002/0128680 A1 | 9/2002 | Pavlovic |
| 2002/0143362 A1 | 10/2002 | Macoviak et al. |
| 2002/0169472 A1 | 11/2002 | Douk et al. |
| 2003/0130685 A1 | 7/2003 | Daniel et al. |
| 2004/0093015 A1 | 5/2004 | Ogle |
| 2004/0153118 A1 | 8/2004 | Clubb et al. |
| 2005/0021075 A1 | 1/2005 | Bonnette et al. |
| 2005/0021152 A1 | 1/2005 | Ogle et al. |
| 2005/0209631 A1 | 9/2005 | Galdonik et al. |
| 2006/0030876 A1 | 2/2006 | Peacock, III et al. |
| 2007/0038226 A1 | 2/2007 | Galdonik et al. |

FOREIGN PATENT DOCUMENTS

| | | |
|---|---|---|
| EP | 1226795 A2 | 7/2002 |
| GB | 2020557 A | 11/1979 |
| JP | 2001-259025 A | 9/2001 |
| JP | 2002-355247 A | 12/2002 |
| WO | 9847447 A1 | 10/1998 |
| WO | 9912478 A1 | 3/1999 |
| WO | 0016705 A1 | 3/2000 |
| WO | WO 02/055146 | 7/2002 |

OTHER PUBLICATIONS

Fiber Innovative Technology: biocomponent and specialty fibers; FIT Capabilities; hrrp://web.archive.org/web/20010217040848/http://www.fitfibers.com/capabilities.htm (Feb. 17, 2001).*

Fiber Innovation Technology: biocomponent and specialty fibers; FIT Products; http://web.archive.org/web/20010408003529/http://www.fitfibers.com/product.htm.*

Fiber Innovation Technology: biocomponent and specialty fibers; FIT products http://web.archive.org/web/20110408003529/http://www.fitfibers.com/product.htm; (Apr. 8, 2001).*

U.S. Appl. No. 10/414,909, filed Apr. 16, 2003, Ogle.

U.S. Appl. No. 10/781,503, filed Feb. 18, 2004, Ogle et al.

Fasseas et al., "Distal protection devices during percutaneous coronary and carotid interventions," current Controlled Trials in Cardiovascular Medicine, vol. 2, No. 6, Dec. 2002, 5 pages.

"Smart suture is first application of novel MIT polymer," from website http://web/mit.edu/newsoffice/nr/2002/langer-suture.html, Apr. 25, 2002, 3 pages.

Reichenspurner et al., "Particulate emboli capture by an intra-aortic filter device during cardia surgery," The Journal of Thoracic & Cardiovascular Surgery, vol. 119(2), Feb. 2000, pp. 233-241.

Harringer et al., "Capture of particulate emboli during cardiac procedures in which aortic cross-clamp is used," The Society of Thoracic Surgeons, vol. 70, 2000, pp. 1119-1123.

Office Action for Japanese Patent Application No. 2006-521136, dated Dec. 15, 2009, and best available English translation (letter from Japanese associate reporting the Office Action).

Supplementary search report for European Patent Application No. 0477837, dated Nov. 16, 2009.

Vaughn et al., "Expanded Surface Area Fibers: A Means for Medical Product Enhancement, " Journal of Industrial Textiles, 2001; 30(4):303-310.

\* cited by examiner

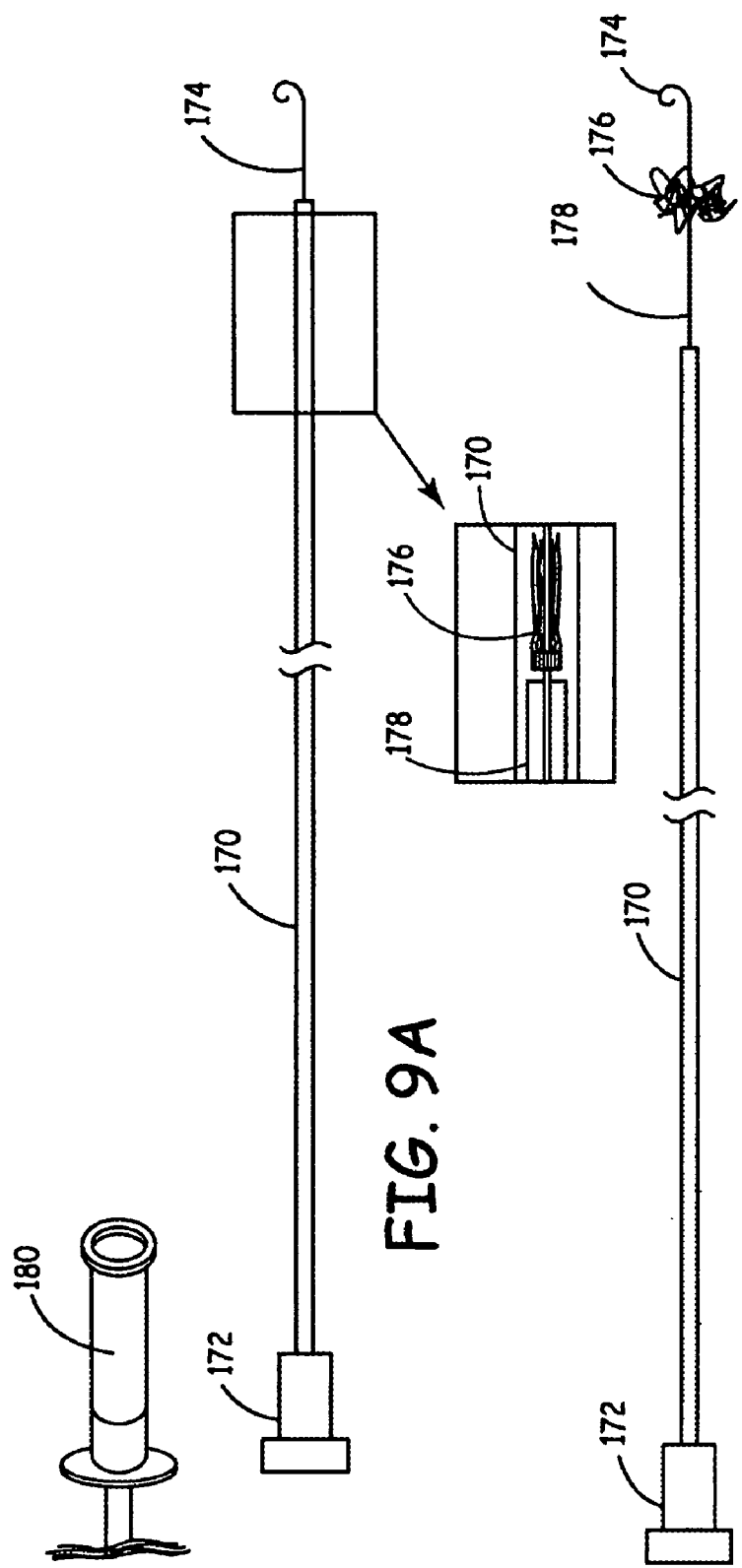

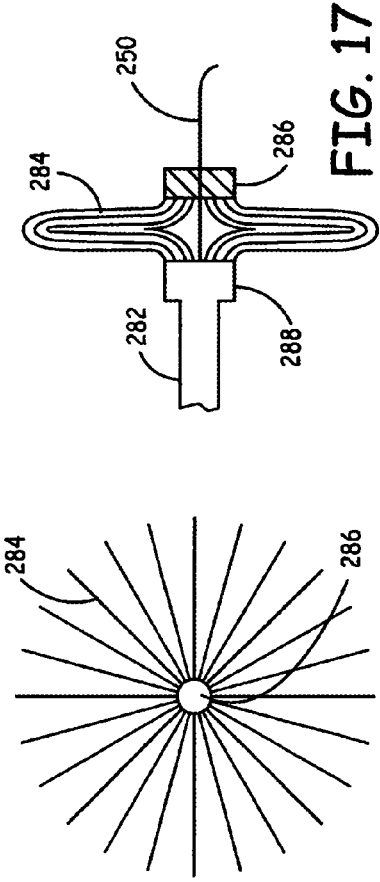
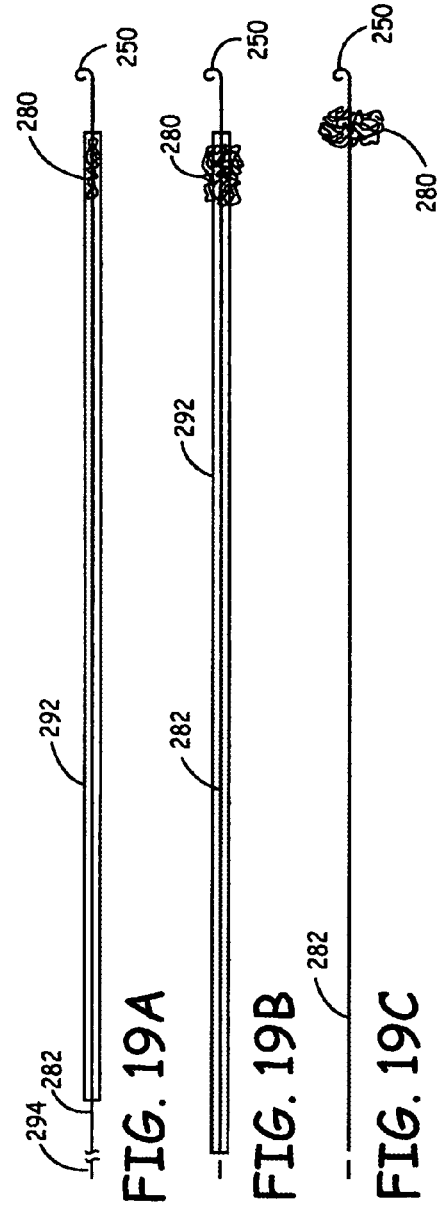
FIG. 17
FIG. 18
FIG. 19A
FIG. 19B
FIG. 19C

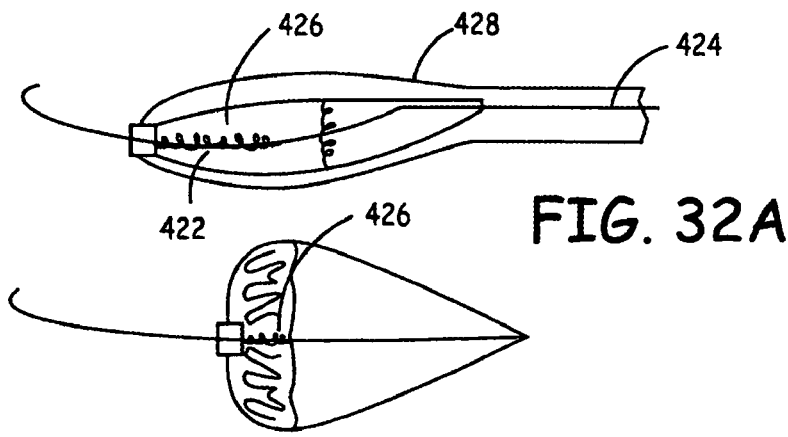
FIG. 32A
FIG. 32B
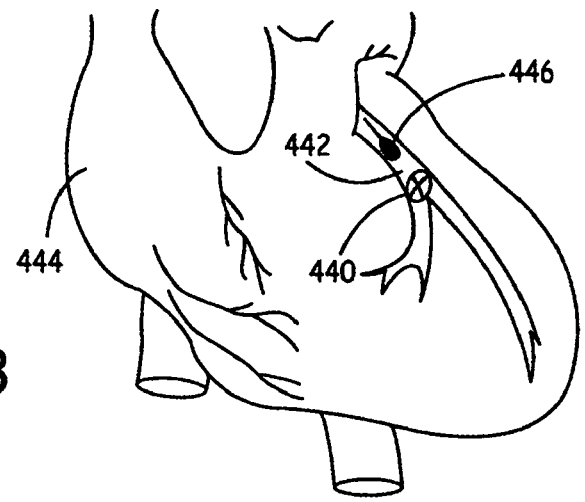
FIG. 33

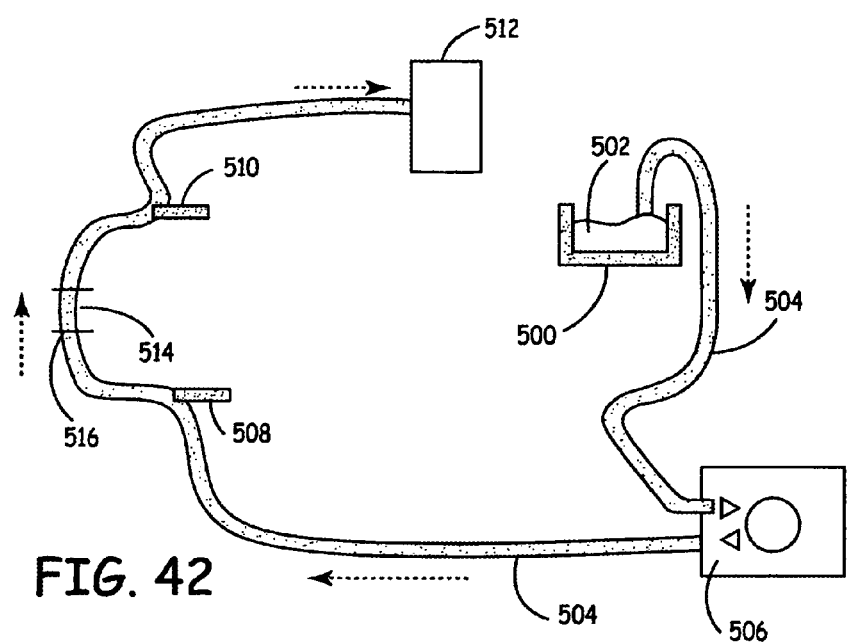
FIG. 42
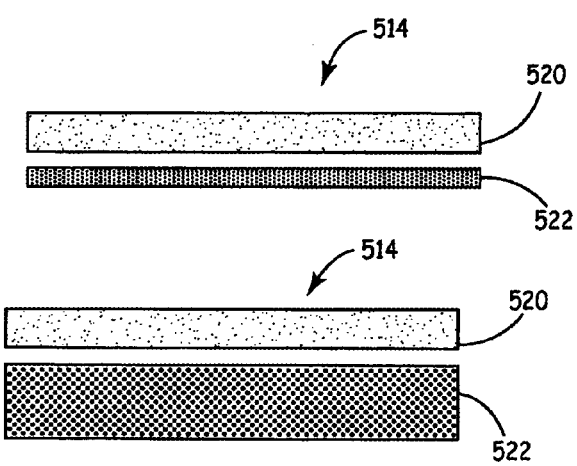
FIG. 43
FIG. 44

FIBER BASED EMBOLISM PROTECTION DEVICE

CROSS REFERENCE TO RELATED APPLICATIONS

This application claims priority to U.S. provisional patent application Ser. No. 60/489,044, filed Jul. 22, 2003 to Ogle et al., entitled "Embolism Protection System," incorporated herein by reference.

FIELD OF THE INVENTION

The invention relates to a device and corresponding systems for preventing blockage of flow of blood or other bodily fluids to distal organs or other distal vessels. In particular, the invention relates to devices suitable for placement within a vessel, such as a blood vessel to trap occlusions, such as emboli, for their dissolution or removal, as well as related methods.

BACKGROUND OF THE INVENTION

An embolus can be any particle comprising a foreign or native material, which enters the vascular system or other vessel of the body with potential to cause occlusion of blood flow. Emboli can be formed from aggregates of fibrin, blood cells or fragments thereof, collagen, cholesterol, plaque, fat, calcified plaque, bubbles, arterial tissue, and/or other miscellaneous fragments. Most emboli lodge in the narrowing regions of medium size blood vessels that feed the major organs. Loss of blood flow to surrounding tissue causes localized cell death or microinfarcts. Cerebral microinfarcts can cause stroke leading to confusion, disturbance of speech, paralysis, visual disturbances, balance disturbances and even death (5). In the heart, emboli can cause myocardial infarcts, i.e. heart attacks.

Disease states including arteriosclerosis and deep vein thrombosis, aging and even pregnancy can cause build up of plaque and fibrin on vessel walls. Anything which loosens or breaks up this plaque can generate emboli. The clinical ramifications of emboli are staggering. Emboli generated from arteriosclerosis of the carotid artery alone cause 25% of the 500,000 strokes that occur yearly in the United States (2002 American Heart Association And Stroke annual statistics). Ironically, the surgical interventions used to remove or bypass the plaque of arteriosclerosis (e.g., balloon dilatation angioplasty, endarterectomy, bypass grafting and stenting) can themselves disrupt plaque. One of the most common cardiovascular interventions is coronary artery bypass grafting (CABG). Historically, 10-20% of all CABG interventions generate emboli large enough to cause myocardial infarcts. This is particularly true when the graft used is of saphenous vein origin. But CABG is not the only procedure with potential to generate emboli. In fact, doppler ultrasound shows evidence of microembolization in almost all cardiac intervention cases. Of the over 1.8 million intervention procedures performed annually, greater than 10% result in neurocognitive disturbance and/or ischemic event (8). These impairments are frequently short term, but can be permanent.

Ten percent is currently considered an acceptable complication rate, however as the number of procedures continues to grow (15-35% increase annually depending on specific procedure (Medical And Healthcare Marketplace Guide, 17th Edition Volume 1, Research Reports 2001-2002.)) the total number of patients affected grows. As this number increases so does patient care spending. Approximately $2.5 billion is spent annually on patients undergoing percutaneous endovascular procedures. The average stay for patients without adverse embolic outcomes is 8.6 days, while patients with severe adverse outcomes stay an average of 55.8 days (1, 3). Estimating the average hospital day care cost at $1500/day, extended stays due to embolic events cost greater than $60,000 per patient. While daunting, this figure fails to include the social and financial burden placed on family members upon hospital release. In summary, embolic events complicating percutanuous endovascular procedures cause high rates of clinically observed neurological disturbances and cardiovascular disease, decreased quality of life and increased patient care spending. Thus, there is a significant clinical need for effective prevention of adverse embolic events.

A significant reason for ischemic injury during percutaneous procedures can be generation of emboli which block smaller distal vessels. One approach to curb this complication has been to use pharmacological therapies during the time of the intervention. Limited therapeutic success has been reported with the use of calcium channel blockers, adenosine, and sodium nitroprusside (Webb, J G, Carere, R G, Virmani, R, Baim, D, Teirstein, P S, Whitlow, P, McQueen, C, Kolodgie, F D, Buller, E, Dodek, A, Mancini, G B, & Oesterle, S: Retrieval and analysis of particulate debris after saphenous vein graft intervention. *J Am Coll Cardiol* 2000, 34:468-475.). Glyoprotein IIb/IIIa inhibitors have been used for percutaneous coronary interventions to reduce platelet aggregation, but also fail to show meaningful long term clinical benefit. (Mathew, V, Grill, D E, Scott, C G, Grantham, J A, Ting, H H, Garratt, K N, & Holmes, D R, Jr. The influence of abciximab use on clinical outcome after aortocoronary vein graft interventions. *J Am Coll Cardiol* 1999, 34:1163-1169 and Mak, K H, Challapalli, R, Eisenberg, M J, Anderson, K M, Califf, R M, & Topol, E J: Effect of platelet glycoprotein IIb/IIIa receptor inhibition on distal embolization during percutaneous revascularization of aortocoronary saphenous vein grafts. EPIC Investigators. Evaluation of IIb/IIIa platelet receptor antagonist 7E3 in Preventing Ischemic Complications. *Am J Cardiol* 1997, 80:985-988.) Lack of benefit may be attributed to the way in which these emboli are generated. In most cases embolization develops from physical disruption of fibrotic plaque. Thus the mechanism of therapeutic embolic protection specifically targeted at prevention of platelet aggregation and blood clotting has little effect on these already-formed, embolizable plaques.

Cardiac Surgery

Each year there are approximately 800,000 cardiac surgical cases, which involve cardiopulmonary bypass (CPB) worldwide. Of these cardiac surgical cases, approximately 48,000 suffer stroke and nearly 300,000 experience some neurocognitive disturbance. This is a significant clinical problem. These complications are due in large measure to CPB-generated emboli. The average number of emboli measured by Trans Cranial Doppler (TCD) in patients undergoing cardiopulmonary bypass is 183 (range 3-947). The majority of emboli end up in the very distal cerebral tree, the terminal arterioles and capillaries causing microinfarctions, (i.e., loss of blood to surrounding tissue). Pathological evaluation of affected tissues reveals sausage-shaped arterial dilatations known as SCADs. Cerebral microinfarctions can cause confusion, disturbances of speech, paralysis, visual disturbances, balance disturbances and other neurological deviations. These impairments are frequently short term but can be permanent.

Cardiology and Endovascular Intervention

Many clinical procedures can result in emboli including, for example, coronary, carotid, and peripheral interventions. (8) In these cases, particulate matter, including, for example, plaque, debris and thrombus, can form emboli distal to the site of intervention. As a result, blood flow to the distal vascular bed can be diminished and periprocedural end-organ ischemia and infarction can result. Distal embolization of large particles produced at the time of such interventions as balloon inflation or stent deployment may obstruct large, epicardial vessels, and smaller particles (as small as 15-100 microns) can cause microinfarcts and/or myocardial infarctions and left ventricular dysfunction. (8) Myocardial infarction refers to the death of a section of myocardium or middle layer of the heart muscle. Myocardial infarction can result from at least partial blockage of the coronary artery or its branches. Blockage of capillaries associated with the coronary arteries can result in corresponding microinfarctions/microinfarcs.

Renal Interventions

Surgical procedures for the treatment of renal artery stenosis can also generate emboli. There is clinical evidence to suggest that 36% of those treated suffer arteriooloar nephrosclerosis caused by atheroemboli. Five-year survival of patients with atheroembolic events is significantly worse than of patients without atheroemboli (54% vs. 85% respectively) [Krishmamurthi et al. J Urol. 1999, 161:1093-6]. These patients could also benefit from distal protection devices.

Emboli and Infection

Foreign material in the stream of flow can cause turbulence or low flow. Such flow conditions have been shown to increase rates of infection. Thrombus not only generates emboli, but also increases the risk of infection. (9)

It is evident that a wide variety of embolic events cause high rates of clinically observed symptoms, decreased quality of life and increased patient care spending.

SUMMARY OF THE INVENTION

In a first aspect, the invention pertains to an embolism protection device comprising biocompatible fibers, a fiber support connected to the fibers and an actuating element operably connected to the fiber support. The fiber support has a first configuration in which the fibers are confined within a narrow profile configuration and a second configuration in which an end of the fibers is constrained while the center of the fiber is unconstrained with respect to the narrow profile. The actuating element controls transition of the fiber support between the first configuration and the second configuration.

In another aspect, the invention pertains to an embolism protection device comprising a biocompatible surface capillary fiber, a guidewire and a fiber support structure connected to the guidewire. At least one end of the surface capillary fiber is secured to the fiber support. The surface capillary fiber has a configuration to fill a lumen surrounding the attached end of the fiber with the lumen having a diameter corresponding to that of a human vessel. An embolism entrapment system can comprise a hypotube having a central lumen, the embolism protection device, wherein the guidewire has a diameter appropriate to pass through the central lumen of the hypotube. The embolism entrapment system can further comprise a treatment structure suitable for delivery over the hypotube.

In a further aspect, the invention pertains to a method for removing emboli from a patient's vessel, the method comprising placing an embolism entrapment device within a vessel of a patient. The embolism entrapment device comprises a plurality of fibers attached to a fiber support structure, and the fiber support structure is attached to a guidewire. The fibers have a configuration with fibers free to fill the lumen of the vessel.

In addition, the invention pertains to an embolism protection system comprising a hypotube having a distal end and a proximal end, an embolism protection device and a guidewire. The embolism protection device is attached at a first end to the distal end of the hypotube, and the guidewire is attached at a second end of the embolism protection device. The guidewire extends through a central channel of the hypotube.

Furthermore, the invention pertains to a method for forming an embolism protection device. The method comprises fastening a plurality of surface capillary fibers at an attachment location to form a fiber support structure that engages a guidewire with an appropriate diameter to pass within a human patient's vessel.

BRIEF DESCRIPTION OF THE DRAWINGS

FIG. 9 is a schematic perspective of a system to load the embolism protection device with therapeutic agent at the time of procedure, shown prior to delivery in view A and following delivery in view B.

FIG. 17 is a side view of the embolism protection device of FIG. 16 following deployment.

FIG. 18 is a front view of the deployed embolism protection device of FIG. 17.

FIG. 19 is a schematic side view of the integrated system of FIG. 14 depicting the deployment of the embolism protection device with view A showing the device within a sheath, with view B showing the device free from a sheath prior to deployment, and with view C showing the deployed device.

FIG. 32A is a schematic side view of an embolism protection device being deployed from a sheath on a guide wire.

FIG. 32B is a schematic side view of the embolism protection device of FIG. 32A following deployment showing the device connected at a fixed point to the guide wire.

FIG. 33 is a schematic view of an embolism protection device deployed in a coronary artery.

FIG. 42 is a diagram showing an in vitro flow loop.

FIG. 43 is a schematic cross section of a device with a SCF fiber matt associated with a mesh, such as a fabric mesh, prior to contact with an aqueous environment.

FIG. 44 is a schematic cross section of the device of FIG. 43 following contact with an aqueous environment leading to the expansion of the fibrous component.

DETAILED DESCRIPTION OF THE INVENTION

Figure 1:
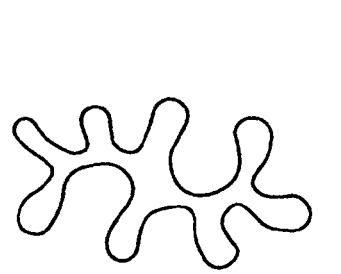
FIG. 1 is a schematic cross section of the surface capillary fibers (SCF).

Improved embolism protection devices described herein generally comprise a fiber or a plurality of fibers within structures that when deployed effectively fill the lumen of a patient's vessel without blocking desired flow through the vessel. In some embodiments, the fibers have surface capillaries that provide desirable properties with respect to enhanced filtration of bodily fluids. In general, the fibers are bound into a structure to provide a desired form for the device. In some embodiments, a portion of the fiber can extend within the lumen of the vessel from a support portion of the structure at which the fiber is bound. In particular, a plurality of fibers can be bound in a bundle with the number of fibers within the bundle being selected to provide the desired effective pore size for flow through the plurality of the deployed fibers. At deployment, the fibers can extend from the narrow profile to fill the lumen of the vessel.

A deployment instrument generally is used to deliver the embolism protection device. The deployment instrument generally holds the embolism protection device in a narrow profile for deployment through the vessel in a less invasive procedure. Improved deployment devices can involve an integrated system with a guidewire, a hypotube and embolism protection device integrated together. In some embodiments, the relative longitudinal motion of the guidewire and the hypotube can be used to actuate the deployment of the embolism protection device. While in some embodiments, the hypotube has an outer diameter approximately the same as a standard guidewire, the hypotube can have other outer diameters including larger outer diameters, and the hypotube can be formed from a variety of biocompatable materials, such as metals and polymers described below, or combinations thereof. In one embodiment of particular interest, a fiber support binds the fibers at two ends, and at deployment the two ends are drawn together to push the center of the fiber between the two ends out across the vessel lumen. The fibers are selected to have a length to extend appropriately within the lumen of the patient's vessel.

Improved embolism protection devices herein generally can reproducibly fill the lumen of a vessel without applying harsh forces against the vessel or leaving gaps past which the emboli can travel. In particular, portions of the fibers within the devices can contour themselves along the surface of the vessel even if the vessel has irregular surfaces. The configuration and density of the fibers can be selected to provide a desired effective pore size for flow past the device. In general, the fibers can be used alone or combined with other polymer compositions. For example, copending U.S. patent application Ser. No. 10/414,909 to Ogle, entitled "Embolism Protection Devices," incorporated herein by reference, describes grafted hydrogel polymers on fibers. With respect to the improved devices herein, in some embodiments, the fibers are surface capillary fibers (SCF fibers), which can provide an enhanced filtering effect as a result of the surface properties of the fiber. Thus, desirable embolism protection devices can be formed from SCF fibers.

Some embodiments of the embolism protection devices herein provide for improved approaches for delivering an embolism protection device, especially in conjunction with additional vessel treatment devices that can be deployed with desired embolism protection supplied by the embolism protection device. In some embodiments, the devices comprise a guide wire integrally incorporated into the support structure and delivery device. In these embodiments, the embolism protection device remains tethered to at least a portion of the delivery device until the embolism protection device or a portion thereof is removed. With the embolism protection device in a narrow profile for deployment, the guide wire can be used to deploy the embolism protection device down stream from an occlusion. In particular, the distal end of the guide wire can be brought past the occlusion from upstream in the vessel, and the embolism protection device is directly deployed on the guide wire past the same occlusion.

The guide wire used to deliver the device can similarly be used to actuate the deployment of the embolism protection device from a low profile delivery format to a fully deployed format filling the vessel lumen. Specifically, the embodiment of the embolism protection device is incorporated into a structure with an integrated actuating device comprising a hypo tube and a very thin guide wire. Longitudinal motion of the hypo tube relative to the guide wire can be used to deploy the embolism protection device. Once the embolism protection device is deployed down stream from the occlusion, the deployed device is in position to collect emboli that may be generated when the occlusion is treated. The embolism protection device is then appropriately placed for the collection of any emboli resulting from the treatment of the occlusions. The integrated actuating device can have an outer diameter comparable to a standard guide wire such that other devices, such as treatment devices used to treat occlusions, can be delivered along the integrated actuating device like a standard guide wire. Specifically, a treatment device, such as a balloon catheter for performing balloon angioplasty and/or a vascular stent, can then be delivered over the same integrateed actuating device as if it were a guide wire to the location of the occlusion to open the occlusion. Following use of the treatment device, the embolism protection device can then be removed with the trapped emboli through the opened vessel along with the integrated actuating device and other components of the device.

Improved medical devices and corresponding systems to capture and/or remove/dissolve emboli and similar particles can incorporate one or more surface capillary fibers. Such structures can entrap emboli either in the surface capillaries and/or between a plurality of the fibers or different portions of the same fiber. The SCF fibers are generally formed from biocompatible polymers. Suitable polymers include, for example, polyesters. Some suitable polymers resume a memory shape upon exposure to a stimulus such as heating to body temperature. The devices can further comprise a bioactive agent, such as an agent that is effective to dissolve the emboli. Generally, the embolism protection device is removed following an appropriate period of time to effectively remove any emboli within the device. The embolism protection device generally is used to control emboli during and/or following a medical procedure, although the devices can be used to protect against emboli from natural events or injuries especially in susceptible individuals.

An embolus as used herein refers broadly to a particle, besides living cells, in a vessel within a mammal having a diameter of at least about 5 microns. For this determination, the diameter is considered the largest distance between two points on the surface of the particle. Thus, emboli would encompass emboli within the blood as well as kidney stones and the like. Vascular emboli are thought to be composed almost exclusively of clotted blood. Arterial emboli generated in aortic surgery or endovascular intervention can be composed of other components, but it is generally believed that they nearly all contain some component of fibrin. See, for example, Reichenspurner et al., "Particulate emboli capture by an inter-aortic filter device during cardiac surgery," J. Thorac. Cardiovasc. Surg. 119(2):233-241 (February 2000), Harringer, "Capture of particulate emboli during cardiac procedures in which aortic cross-clamp is used," Ann. Thorac. Surg. 119(2):701119-23 (February 2000) and Webb, "Retrieval and analysis of particulate debris after saphenous vein graft intervention," J. American College Cardiol. 34(2): 468-475 (1999), all three of which are incorporated herein by reference. In some embodiments, embolism protection devices, described herein, can protect the patients in at least one of three ways: first by filtering emboli, second by dissolving entrapped emboli and third by bathing the distal myocardial bed or other down flow portion of a vessel with a beneficial bioactive agent, such as an embolism dissolving compound, for example, tissue plasminogen activator (tPA), to help resolve emboli which have become impacted there.

The embolism protection device can be delivered, for example, out of a medical implement (catheter or syringe) into the desired vessel, such as a vascular vessel. The device may or may not be covered by a sheath to protect the device as it passes through the vessel until it is ready to be deployed. In some embodiments, the material of the device can dilate upon opening in the patient's blood vessel to circumferentially encompass/fill the vessel. In some embodiments, this dilation may be facilitated by a tube or element to tamp down the device. The device may or may not remain connected to the delivery device. In embodiments that remain tethered, the expanded device contacts the vessel walls to fill the lumen of the vessel, but the contact with the vessel walls does not need to anchor the device. In embodiments in which the embolism protection device does not remain anchored to the delivery device, the expansion of the device can anchor the device within the vessel due to contact with the vessel wall.

In some embodiments, the device can have the flexibility to conform to the geometry of the vessel. The materials, matrix and structure of the device can be selected to have porosity that would allow blood elements, such as white blood cells (about 7-20 microns), red blood cells (8-9 microns) and platelets (2-4 microns), yet collects emboli. In contrast, emboli generally range in size with diameters from about 20 microns to about 3.5 mm, in some embodiments from about 45 microns to about 1000 microns and in further embodiments from about 50 microns to 200 microns. A person of ordinary skill in the art will recognize that additional ranges of emboli within the explicit ranges are contemplated and are within the present disclosure. Thus, in some embodiments of interest, the trapping of emboli with a size larger than about 45 microns to about 50 microns would be beneficial.

In some embodiments, desired embolism protection devices can comprise SCF fibers as the only structural component. For example, the device can comprise a single fiber or a plurality of fibers, which can be multiple entwined fibers, woven fibers, bundled fibers, separately attached fibers or the like. This fiber or fibers can be configured to anchor within a vessel within the patient to filter the flow. However, in many embodiments of interest, the SCF fibers are combined with one or more other material to form the embolism protection device. These other materials can be, for example, tissue, polymers, ceramics and/or metals. Specifically, in some embodiments, the embolism protection devices described herein generally comprise a fiber matrix that is placed in a vessel to form a unique structure. SCF fibers are specialty fibers, which can incorporate unique fabrication technology, that produces fibers with several advantages over existing round fibers. The use of SCF in other medical devices is described in copending U.S. patent application Ser. No. 10/781,503 to Ogle et al., filed on Feb. 18, 2004, entitled "Medical Article Incorporating Surface Capillary Fiber," incorporated herein by reference.

SCF fibers are characterized by surface channels or capillaries formed within the surface of the fiber. Surface capillaries are characterized by having a portion of the capillary exposed at the surface of the fiber along the length of the fiber. The surface capillaries result in significant increase in the surface area of the fibers relative to fibers with a smooth surface and the same diameter. The surface capillaries generally run along the length of the fiber. In some embodiments, the surface of the fiber has a plurality of surface channels or capillaries along the length of the fiber. An SCF fiber can have surface channels that essentially make up a large fraction of the bulk of the fiber such that little if any of the interior mass of the fiber is not associated with walls of one or more surface capillaries.

In particular, the SCF fiber substrate can be formed with a relatively complex cross-sectional geometry. In some embodiments, the geometry of the fibers used in particular medical devices have surface capillaries that can move relatively large amounts of fluid at significant rates. Suitable fibers include commercially available 4DG™ fibers (Fiber Innovation Technology, Inc., Johnson City, Tenn.) but would also include new advanced geometries to provide for greater fluid transport or absorption or wetting capabilities. In particular, geometries can be selected to be particularly advantageous for the particular application. Suitable approaches for the manufacture of the SCF are described in, for example, U.S. Pat. No. 5,200,248 to Thompson et al., entitled "Open Capillary Structures, Improved Process For Making Channel Structures And Extrusion Die For Use Therein," incorporated herein by reference. Alternative fiber structures are described below.

Furthermore, the selection of the polymer composition for the fiber can provide further flexibility to the properties of the fiber for a particular application. For example the fiber polymer composition can modulate the hydrophobic or hydrophilic nature of the device, or the polymer may elute controlled released drugs. Furthermore, the fibers can incorporate coatings or the like that can further modify the fiber properties. The polymer composition for the SCF fibers generally can incorporate certain desired properties of medical polymers, such as established biostability, bioerosion, strength, flexibility, and compressibility. In some embodiments, the SCF fibers are 4DG™ fibers, with sizes ranging from about 1.5 denier to about 1000 denier in size. The size of the fibers can influence the mechanical, structural, filtration, compressablilty and fluid dynamic properties of the device. Thus, the selected fiber size may be different for different applications.

Figure 2:
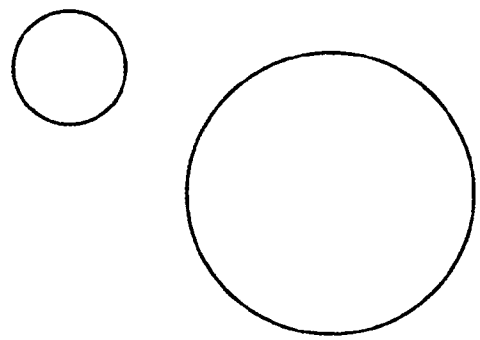
FIG. 2 is a round fiber in comparison to SCF fiber FIG. 1.

SCF can have advantages over existing round fibers in certain embodiments as follows: novel cross-sections, hydrophilic lubricant or hydrophobic treatment, high surface energy, high fluid transport qualities, and increased absorbency and storage capabilities. Each fiber can have a series of grooved channels, which act as a surface capillary system. A schematic cross section of an embodiment of a surface capillary fiber is shown in FIG. 1, with a cross section of two contrasting round fibers shown in FIG. 2. These channels can impart excellent fluid management such that the device can rapidly transfer fluid despite material obstruction. In addition, the channels can be excellent vessels to house the thrombolytic agent; agents such as these are held securely until additional fluid is added (i.e., blood flow in the vessel). And the channels are highly compressible but can have excellent conformational memory. Thus, a small unobtrusive device can be fabricated for gentle insertion, which resumes its channel conformation, when deployed. The surface channels can have various sizes, shapes and configurations, as described further below. Furthermore, the flexibility of the fibers provides a conformable and less injurious interaction with the vessel wall. This improved interaction with the vessel wall can improve filter effectiveness without damaging the vessel wall by decreasing gaps for emboli to bypass the device. These fibers can help facilitate, excellent flow maintenance (even after embolic entrapment), entrapment of very small particles (~40 um) and facilitate embolic dissolution by these devices.

Furthermore, the embolism protection device can comprise additional polymer structures and/or structures of other materials, such as fiber anchors, delivery devices, retrieval devices, components thereof or combinations thereof. to introduce desired properties to the device. Additional polymers, such as polyesters, polylactic acid, PGA, polypropylene, nylon, polyurethanes, modified polyurethanes, polycarbonates, copolymers thereof or a polymer blends thereof can provide mechanical strength to the device and/or a composite material. The embolism protection device can comprise one or more additional materials, as desired, to provide particular structural or functional features. For example, the outer surface can comprise a material, such as an adhesive or a fabric that expands with the fibers but contributes to anchoring of the device to the wall of the vessel. Some embodiments could contain multiple materials for modifying the composition and/or the structure, as desired.

In some embodiments, the material of the device or a portion thereof can be selected to slowly resorb over time. In these embodiments, the device can be left within the patient rather than being removed. In some embodiments, even if a portion of the resorbable material were to dislodge from the aggregated material of the device, the resorbable material can still have the same porosity to be able to filter while providing flow further up the vascular tree. Resorbable materials within the embolism protection device could be tuned to dissolve over a time range from a very short time to a very long time after surgery, as desired. In some embodiments, an imaging approach can determine the presence of calcified plaque trapped within the embolism protection device, which would then be removed surgically.

While some embodiments involve the release of the embolism protection device into a patient's vessel, in other embodiments, the embolism protection device remains connected with the delivery apparatus. In particular, the embolism protection device can comprise fibers bound to the delivery apparatus. For example, the fibers can have a shape memory such that the fibers extend into the lumen of the vessel once they are released from a constrained configuration. The restoration of the shape can be assisted by the heating of the fibers to body temperature. A cannula/sheath or the like can cover the fibers during delivery to hold them in a constrained configuration. The cannula can be withdrawn to release the fibers once the embolism protection device is in position.

In some embodiments, the embolism protection apparatus comprises an integrated actuating apparatus with a hypo tube having a central lumen and a thin guide wire within the central lumen of the hypo tube. The relative longitudinal movement of the hypo tube and the guide wire can provide for release of the embolism protection device, for example, by uncovering the embolism protection device. In some embodiments of interest, the fibers are attached at two points along the guide wire and the proximal attachment point is attached to the hypo tube. Then, by displacing the guide wire in a proximal direction relative to the hypo tube, the attachment points are brought together and the fiber between the attachment points tack a configuration projecting into the lumen of the vessel in which the guide wire is located. Thus, the embolism protection device is deployed. The fibers can be SCF fibers to provide desirable properties. The length and other properties of the fibers and the fiber bundle can be selected to provide appropriate filtering properties for the size of the vessel, as described further below.

In some embodiments, a biologically active agent can be released by way of the embolism protection device. For example, the biologically active agent can be released from a reservoir within the embolism protection device either quickly and/or in a gradual fashion. Additionally or alternatively, the embolism protection device can be connected during a procedure to an external source of biologically active agent that is released in a desired dose at or near the embolism protection device. For embodiments in which the embolism protection device comprises a reservoir of biologically active agents, the embolism protection device can also elute a biologically active agent from one or more materials, which could aid in neurological/vascular disease prevention associated with surgery. In some embodiments, the reservoir of biologically active agent is physically trapped within the material such that it is released quickly by expansion of the material upon delivery of the device. In other embodiments, the biologically active agent is eluted gradually by diffusion out of the material from which the device is formed or released gradually by degradation of the material from which the device is formed. In some embodiments, the embolism protection device remains connected to a wire following delivery in which the wire has a small inner lumen through which the biologically active agent is delivered. The delivery through the wire can be controlled both in terms of release time and rate, for example, with a syringe, peristaltic pump or the like.

In some embodiments a biologically active agent may be associated with the EPD with chemical and/or physical approaches. This association can be accomplished by many approaches such as, covalent bonding, for example, involving appropriate reactive functional groups and/or photochemical bonding, absorption or otherwise incorporated into a material, adsorption as a physical surface treatment, and/or association to an antibody linkage. Generally, the association can be accomplished such that the agent remains active following association with the material. In general, the association can be performed such that the biological agent remains bound, or the biological agent can be eluted from the device. Similarly, the association can be performed to result in a combination of eluted and non-eluting-bonded biologically active agents. It is also further envisioned that agent could be bound at the point of use. This could be accomplished by pre-bonding an antibody that is reactive to the biological agent and at the time of use intervention procedure delivering an excess of agent to the device.

Medical devices incorporating SCF fibers can be effective for the delivery of bioactive agents in the vicinity of the medical device. By incorporating the bioactive agents within the surface capillaries of the fibers, the volume of the bioactive agent can be significantly greater than can be readily associated with a conventional fiber surface of the same length. The form of the bioactive agent can be selected to yield the desired release profile. For gradual release of the bioactive agent, the agent can be combined with a controlled release agent. In other embodiments, the formation of the bioactive agent can be selected to yield an appropriate release rate over shorter periods of time. The particular contouring of the fiber can similarly influence the release rate due to surface effects.

Suitable bioactive agents can be thrombolytic agents such as tissue plasminogen activator (tPA) or urokinase, or the agents can release mild acid (possibly along with a neutralizing base, such as bicarbonate) or anti-calcification enzymes such as osteopontin to resorb calcific plaque. Release of one or more emboli dissolving agents locally can reduce effects of the emboli. In other embodiments, the device can release $O_2$ and/or sugars to nourish the patient's brain cells. In further embodiments, the device can release vasodilators such as NO or heparin to increase the available $O_2$ transport. In additional embodiments, the device can release growth factor, which could improve healing or create new vessels. In further embodiments, the device can release viral vectors, which transfected the surrounding cell to up regulate the release a polypeptide compound for extended therapy (e.g., tPA). Specifically, for protein/polypeptide based agents, the delivery of a gene (nucleic acid) encoding the agent in a vector, such as a viral vector, to promote in vivo expression of the protein is an alternative to the delivery of the protein itself. Delivery of vectors for desired polypeptides is described further below. The device similarly can be designed to release a plurality of these agents.

With appropriate sizing, the embolism protection device can be applied to any size vessel of a patient. The patient can be any animal, generally a mammal, with particular interest in humans, pets, farm animals and other domestic animals. The devices generally have an ability to conform to irregularly shaped portions of a vessel. Thus, this invention could be used for a vascular surgery to prevent a clot, which could cause paralysis, amputation, surgical vascular intervention, other neurological impairment or death. Due to complications from emboli, such as a thrombus, there is a significant clinical need for effective protection from emboli and resulting embolisms. For example, significant potential applications pertain to coronary intervention following Acute Myocardial Infarct (AMI). These cases can represent 25% of all coronary interventions (as reported at GW Stone Lennox Hill Hospital) due in large part to the commonly thrombus-laden lesions found in AMI patients. Due to the flexibility of some embodiments of devices described herein and the speed at which they can be applied, an embolism protection device can be applied in a wide range of circumstances. In cases such as a broken hip, deployment of the embolism protection device could be pre-formed as an emergency procedure to prevent clot formation in patients with pro thrombotic disease and hence increased incidence of clot formation.

In some embodiments a string/tether/wire can be attached to the device for delivery and/or extraction of the device. This attachment can act to reduce the luminal size of the device upon extraction for some embodiments of the device. In some embodiments, an extraction device, such as a gripper or the like, can be used to facilitate the removal of the embolism protection device by physically compressing the embolism protection device. In some embodiments, the embolism protection device can be integrally incorporated with the delivery device and/or the retrieval device or portions thereof.

Thus, the embolism protection devices described herein can be effective to reduce or eliminate damage resulting from emboli in circumstances in which potential damage may be indicated by the performance of particular medical procedure, from the identification of diseases and/or by injuries to the patient. The material properties of the device provide great flexibility in the design of the device with respect to different potential ways of handling the emboli. Through the use of suitable fibers, the devices can be very versatile with respect to convenience of delivery, conformability to a wide range of vessels and uniform performance in a range of environments. By combining biologically active agents with the devices, the improved structural features can be combined with the ability to deliver treatments to a localized environment.

A number of devices are currently being developed to reduce the embolic events associated, for example, with carotid and coronary procedures. These devices can be categorized into two types of devices: occlusion devices and filters. These devices can be mounted on the same guidewire used to deliver an angioplasty balloon or stent depending on the type of intervention. The device is placed distal to the site of intervention.

Balloon occlusion devices consist of a balloon mounted on the guide wire. During the procedure the balloon is inflated thereby blocking all blood flow at a point distal to the intervention. The catheter is used to aspirate debris generated from the procedure. The benefits of the improved devices described herein include, for example, improved flexibility (in comparison to filter systems) which allows easier access to tight lesions and complex, diseased vessels. They also provide significant protection by preventing even the smallest emboli from proceeding distally. Yet filter devices can also have other issues with respect to their use. For example, the interruption in blood flow in up to 10% of the patients (especially those with contralateral occlusion) may lead to adverse events (Ohki T, Veith F J. Carotid artery stenting: Utility of cerebral protection devices. *J Invasive Cardiology* 13(1): 47-55, 2001). In addition, a second step is needed to flush out and aspirate the emboli. This technique does not allow for angiograms to be taken during the procedure making placement more difficult. Also, expansion of the distal protection balloon can trigger additional embolization, vaso-spasm and even dissection of the vessel.

Other devices currently under development utilize filtration as a mechanism to reduce emboli. Similar to the occlusion device, the filter (size exclusion >80-100 microns) is placed distal to the intervention site where it is expanded. Upon completion of the procedure, it is collapsed trapping some of the particulate matter generated from the procedure. Advantages of the filter approach include continued blood flow throughout the procedure, ability to perform angiography during the procedure, and no flushing step requirement. However, filter devices can have a large crossing profile which makes access to tight or tortuous lesions difficult thereby increasing the likelihood of vessel spasm or dissection. Second, during the procedure, the guide wire generally should be held in precise position to prevent emboli from passing. Also, even with proper positioning the pore size of the filter can allows up to 80% of the smaller particles to pass and the filter material itself has potential to thrombos and release thrombi.

The present devices disclosed herein have advantages with respect to ease of insertions and removal and suitability for native coronary intervention due to their flexibility. This ease of use can shorten surgical times and reduce the incidence of emboli formation through disruption of vessel-associated plaque or tissue. Also, the present devices in some embodiments can conform to complex and asymmetric contours of the vessel wall to reduce the presence of open sites through which emboli can escape. Also, the present devices provide for the removal of emboli through the two dimensional nature of the device which can entrap emboli for removal.

Additional embodiments of improved embolism protection devices with other features are described in copending U.S. patent application Ser. No. 10/414,909 to Ogle, entitled "Embolism Protection Device," incorporated herein by reference.

Structure of Embolism Protection Devices and Corresponding Systems

The embolism protection devices can have various sizes and shapes both with respect to the effective exterior surface before and after deployment and with respect to the arrangement of the materials through the cross section of the structure. In the fiber based embodiments described herein, the outer surface of the device may be only generally defined by extrapolating between neighboring fibers along the outer portions of the structure. The nature of the arrangement of the material across the device generally is formulated to be consistent with the maintenance of flow through the device while capturing emboli over an appropriate size such that they do not flow past the device. Thus, the device can comprise a single fibers that folds to form a particular structure, multiple fibers that are arranged various ways, and the structure can comprise one or more fibers combined with one or more additional materials to form the filtering portion of the embolism protection device. Corresponding systems include tools for the delivery, deployment and/or retrieval of the embolism protection device. Improved integrated systems are described in the following section that can be effectively used with fiber based embolism protection devices as well as other types of embolism protection devices.

The embolism protection device can be designed for unrestrained placement within a vessel of the patient or the embolism protection device can remain attached to the delivery tool. The device can comprise one or more fibers with selected structures and/or the fibers can be manipulated within the structure by combination with additional components. For example, the fibers can be organized into a bundle that is deployed within the vessel. A bundle of fibers may or may not be associated with a fabric cover that mediates the interaction of the fibers with the vessel wall. The embolism protection device can comprise a plurality of domains with one or both of the domains comprising fibers.

With respect to the shape of the exterior of the device, this shape can be, for example, generally spherical, cylindrical, concave, or saddle shaped. A generally spherical or other shaped device may nevertheless have a roughly irregular surface contour about an average overall shape, which can orient and adjust to the vessel inside wall upon expansion. Some representative examples are provided below. Any particular device generally can conform to the specific size and shape of the inside of the vessel following a rough size selection for the device. While the particular device size depends on the size of the particular vessel, an embolism protection device following expansion within the vessel of a human patient general can have a diameter perpendicular to the flow direction from about 50 microns to about 35 millimeters (mm), in additional embodiments from about 100 microns to about 9 mm and in further embodiments, from about 500 microns to about 7 mm. A person of ordinary skill in the art will recognize that additional ranges of device diameters within the explicit ranges are contemplated and are within the present disclosure.

Once the embolism protection device is positioned within a vessel, appropriate flow should be maintained through the device while emboli are trapped. Thus, with respect to the flow direction, the device has controlled porosity. This controlled porosity can be established by the nature of the material and/or by the particular structure. Specifically, the fiber density and fiber structure within the device can lead to an effective distribution of pores such that desired flow is provided while emboli are trapped. In particular, SCF fibers can trap smaller emboli within the surface capillaries, while larger emboli can be trapped along the surface and/or between fibers within the overall embolism protection device structure.

In some embodiments, the device comprises a composite of two structures/materials with different pore sizes from each other. For example, the device can comprise a first material with an average pore size following expansion of the device between about 150 microns and 300 microns to be positioned approximately downstream and a second material with an average pore size of about 50 microns to be positioned approximately upstream. Alternatively or additionally, the polymers can be specifically arranged to have a structure that directly leads to pore sizes with desired sizes one the device expands within the vessel.

In general, the desired filtering properties and corresponding average pore sizes and pore size distributions of an embolism protection device may depend on the particular location of the particular vessel in which it is delivered. However, for many applications it can be desirable to block the flow of a substantial majority of particulates with a diameter of at least about 0.2 mm while allowing the flow of a substantial majority of particulates with a diameter of no more than about 0.001 mm, and in other embodiments, to block the flow of a substantial majority of particulates with a diameter of at least about 0.1 mm while allowing the flow of a substantial majority of particulates with a diameter of no more than about 0.01 mm. A person of ordinary skill in the art will recognize that additional ranges of filtering ability within the explicit ranges are contemplated and are within the present disclosure. A substantial majority of particulates can be considered to be at least about 99 percent.

The embolism protection device can be deployed with a syringe, catheter, cannula, grippers or other convenient approach. Several specific approaches are described herein, and a person of ordinary skill in the art can adapt other delivery approaches based on the teachings herein. In some embodiments, it is desirable to remove the embolism protection device at some period of time following deployment. Since the embolism protection device expands to contact the interior of the vessel walls, it may be desirable to introduce structures that facilitate the removal of the device. If the device remains attached to the delivery tool, the delivery toll can similarly be used to facilitate extraction of the device. In other embodiments, the embolism protection device is left for some period of time within the patient's vessel, and a separate tool can be used to extract the device. In either situation, the device generally is extracted with a tool that reduces or eliminates release of emboli from the device during extraction. For example, for embodiments in which the device remains attached to the deployment tool, the delivery device can comprise one or more tubes, sheaths, rigid extensions, wires, strings, filaments, tethers or the like appropriately positioned for extracting the device. In some embodiments, the strings are placed such that pulling on the string tends to contract the device to reduce or eliminate friction on the vessel wall. For example, the strings can be positioned at or near the outer edge of the device that contacts the vessel wall such that pulling on the string tends to pull the exterior of the device toward the center of the vessel. Tethers and the like also can be useful to maintain an embolism protection device at a delivered position within a vessel. Thus, with a tether or guide wire to maintain the position of the embolism protection device against flow within the vessel, the device may or may not exert significant force against the inner wall of the vessel.

In addition, an extractor device can be positioned with a catheter or the like near the embolism protection device. For example, the extractor can comprise a gripping element that grips the device to reduce its dimensions by physical force such that the embolism protection device can be removed through a catheter or the like. Similarly, an extractor can comprise a sheath or the like. The embolism protection device can be tapered such that an end of the expanded device fits within the sheath. Then, pulling the device relative to the sheath, such as using a tether or the like, can compress the device within the sheath for removal of the device within the sheath from the patient. Similarly, the device can be twisted in a cork-screw type fashion to decrease the diameter of the device due to the torque and the compressible nature of the polymers. Similar approaches can be used for placement of the devices within a sheath for delivery of the device. For embodiments of embolism protection devices intended for removal from the patient, it may be desirable to have a smaller porosity toward the vessel wall relative to the porosity away from the vessel wall to reduce the possibility of emboli escaping from the device during the removal of the device from the patient.

Figure 3:
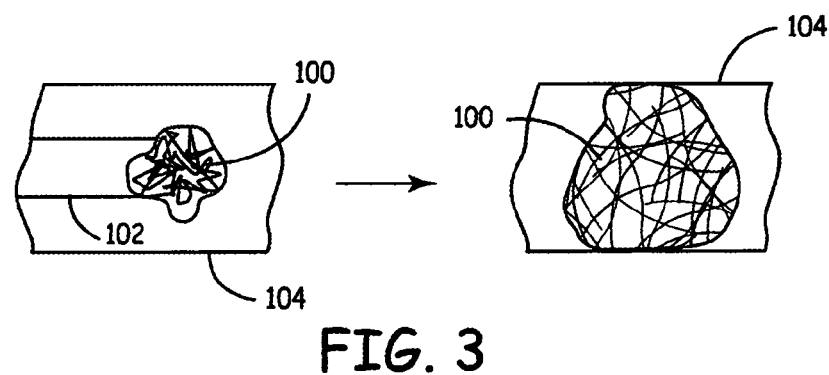
FIG. 3 is a schematic side view of an embolism protection device within a patient's vessel with the left view showing the deployment of the device from a deployment apparatus and the right view showing the device following deployment.
Figure 4:
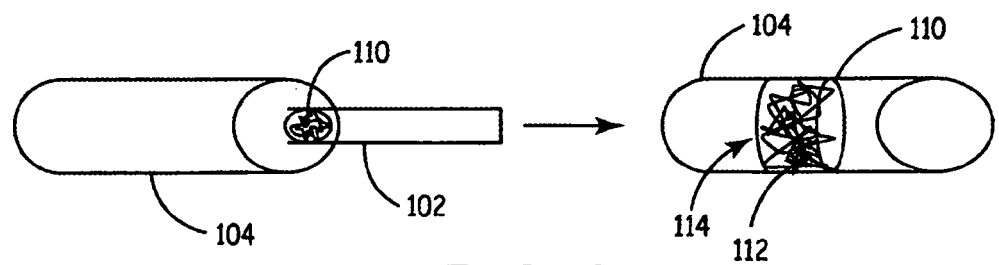
FIG. 4 is a schematic perspective view of an alternative embodiment of an embolism protection device within a patient's vessel with the left view showing the deployment of the device from a deployment apparatus and the right view showing the device following deployment.

Referring to FIG. 3, the left view displays a generally spherical embolism protection device 100 formed from a fiber mesh adjacent a catheter 102 within a vessel 104. The right hand view in FIG. 3 shows device 100 following expansion to fill the lumen of vessel 104. The arrow between the two views indicates a temporal advance over which device 100 expands across the lumen of vessel 104. In this embodiment, device 100 has a random array of fibrous polymer forming the interior of the device 100. The expansion can be driven by a shape memory of the fibers, although other mechanisms are possible. In an alternative embodiment, embolism protection device 110 has a cylindrical shape with a random interior polymer structure 112, as shown in FIG. 4. In this embodiment, device 110 has an outer surface covered with a fabric 114 excluding the flow ends through which the flow of the vessel passes. Referring to further alternative embodiment in FIG. 5, embolism protection device 120 has a generally cylindrical shape with a fiber matrix 122 that is approximately arranged on a grid. The outer surface of the cylinder is covered with fabric 124 with the ends of the cylinder exposed, i.e., free of the fabric. If fabric 124 has a sufficiently open weave, the fabric may also cover the ends of the cylindrical structure.

Figure 5:
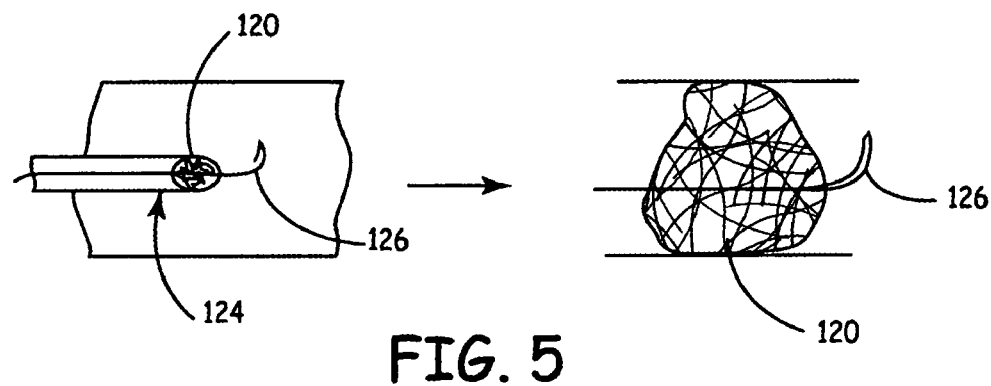
FIG. 5 is a schematic perspective of an alternative embodiment with a fiber matrix being deployed from a sheath using a guidewire.
Figure 6:
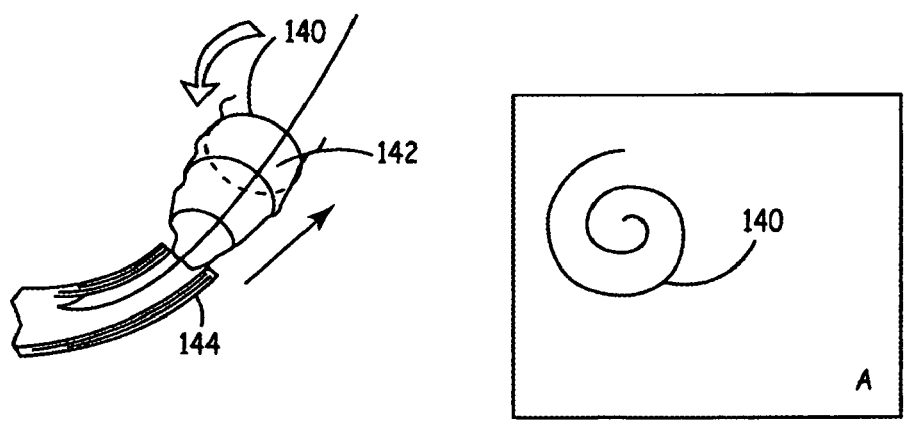
FIG. 6 is a schematic of tools to compress the embolism protection device to allow loading into the sheath of FIG. 5.
Figure 7:
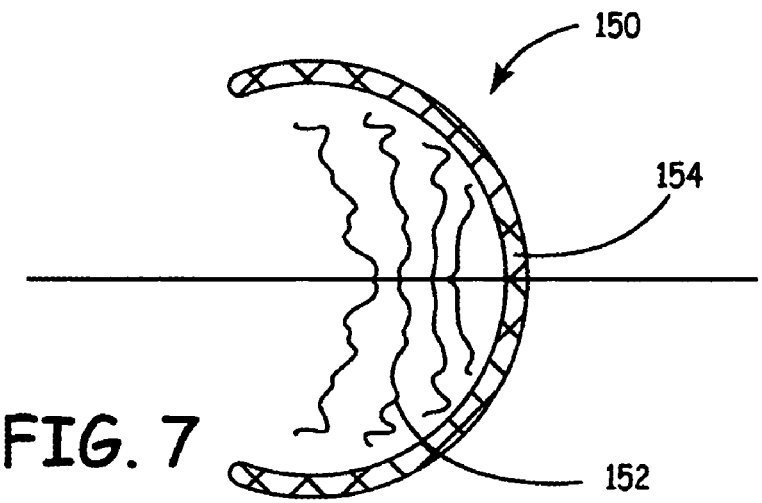
FIG. 7 is a schematic side view of an alternative embodiment of an embolism protection device with two components, comprising a net and fiber matrix.
Figures 8A, 8B:
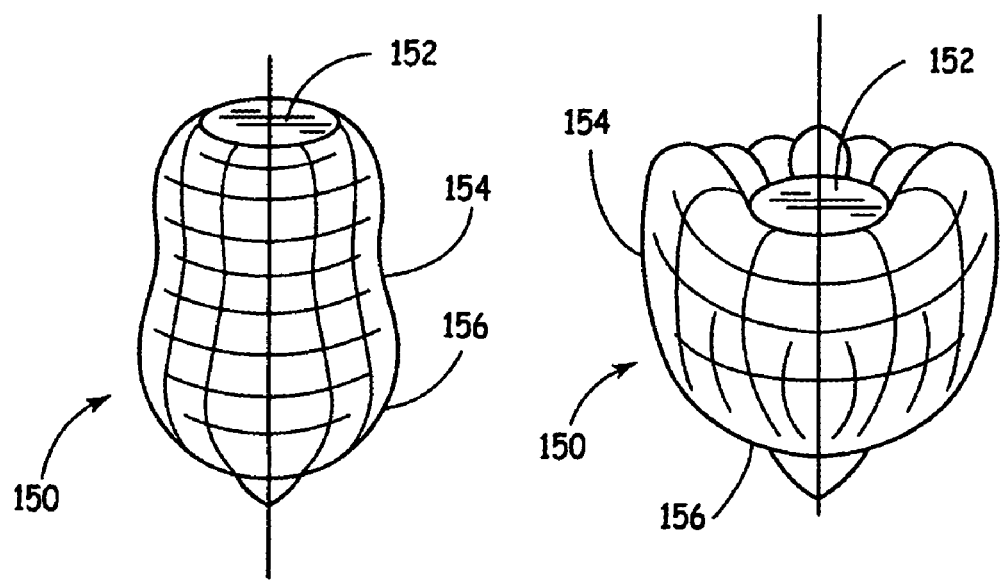
FIG. 8A is a schematic side view of an alternative embodiment of an embolism protection device shown prior to deployment.
FIG. 8B is a schematic side view of an alternative embodiment of an embolism protection device of FIG. 8A shown following the deployment and corresponding expansion of the device.

Other alternative embodiments are shown in FIGS. 5, 6 and 7. In FIG. 5, the device 120 has a fiber matrix that can be delivered with a sheath 124 using a guide wire 126. As shown in FIG. 6, a spiral device 140 (shown in a top view in insert A) can compress a fiber matrix 142 for loading into a sheath 144. A shown in FIG. 7, the embolism protection device 150 comprises a fiber matrix 152 within a mesh 154, such as a fabric mesh. The fiber matrix traps emboli before they reach the mesh such that the emboli do not clog the mesh and flow is maintained through the device. Other views of device 150 are shown in FIG. 8 in which the base 156 of mesh 154 is stiffened to maintain the device integrity following deployment. The compressed configuration is shown in FIG. 8A, and the expanded configuration is shown in FIG. 8B.

As shown in FIG. 9, a drug can be delivered in conjunction with the delivery of an embolism protection device. As shown in FIG. 9A, a catheter 170 extends from hub 172 along guide wire 174. As shown in the insert, embolism protection device 176 is delivered through catheter 170 with hypo tube 178. Hub 172 restricts fluid flow from catheter 170 to prevent unnecessary blood loss. Syringe 180 connects to hub 172 to deliver a bioactive agent/drug through catheter 170, hypo tube 178 and/or guide wire 174. The configuration following the deployment of embolism protection device 176 is shown in FIG. 9B. Various embolism protection device designs can be used along with drug delivery. Embodiments in which a bioactive agent is delivered from the embolism protection device are described further below.

Figure 10A:
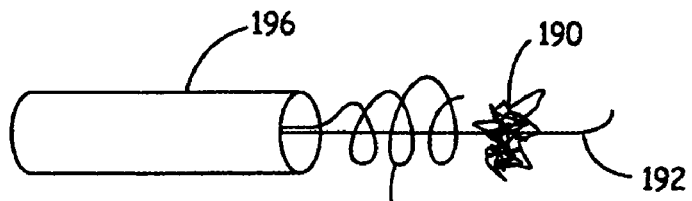
FIG. 10 is a schematic side view of an alternative embodiment of an embolism protection system with mechanical retraction mechanism with view A showing the retraction mechanism prior to engaging the embolism protection device and view B showing the retraction mechanism removing the embolism protection device.
Figure 10B:
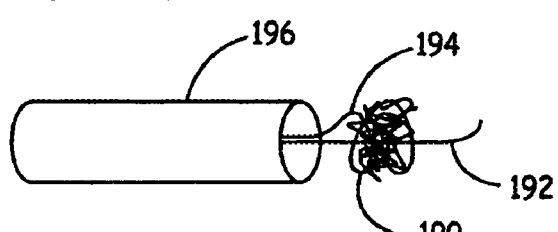

The removal of a compressible embolism protection device is shown in FIG. 10 using a spiral shaped retraction element. Referring to FIG. 10A, a deployed embolism protection device 190 is in a deployed configuration in association with a guide wire 192, although this retraction element can be similarly used if the embolism protection device 190 is deployed in a disconnected configuration within a patient's vessel. Retraction element 194 is delivered through a guide catheter 196. As shown in FIG. 10B, application of torque to spiral retraction element 194 can compress embolism protection device 190 for removal through catheter 196.

Figure 11:
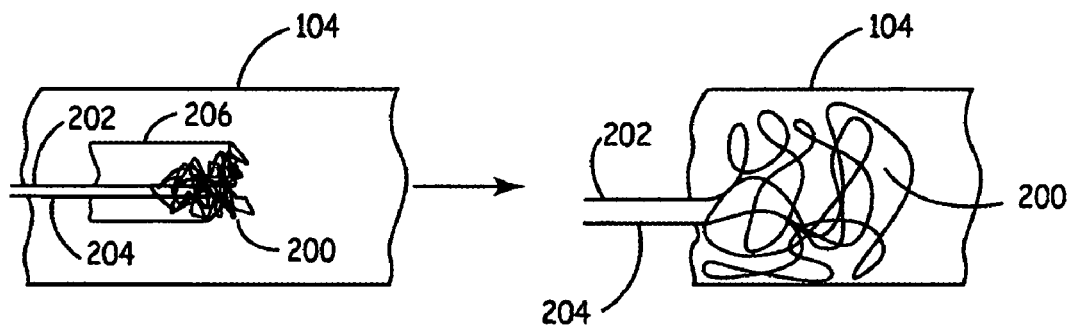
FIG. 11 is a schematic side view of an alternative embodiment of an embolism protection device with a tether to facilitate removal within a patient's vessel with the left view showing the deployment of the device from a deployment apparatus and the right view showing the device following deployment.
Figure 12:
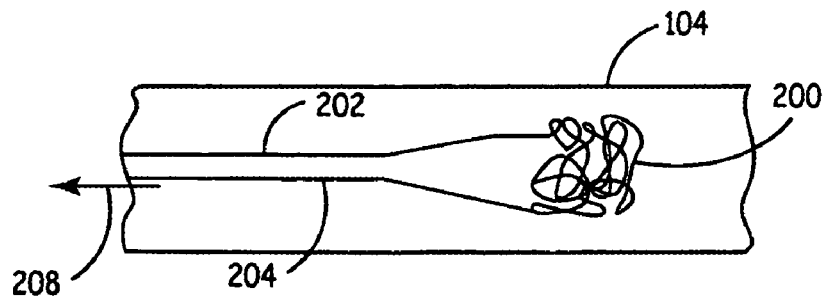
FIG. 12 is a schematic side view showing the use of the tether to remove the device of FIG. 11.

An embolism protection device can comprise a tether or the like to facilitate removal of the device after sufficient time to protect against emboli. Referring to FIG. 11, embolism protection device 200 comprises two strings 202, 204 that tether device 200, although a single string or greater than two strings can be used. Device 200 is shown in an unexpanded configuration in the left side view of FIG. 11 within a catheter or hypo tube 206 and in its expanded form in the right side view of FIG. 11. By providing two strings, pulling on the strings tends to draw the strings together to contract the device if the strings are in a spaced apart attachment on the device. As shown in FIG. 12, tension on strings 202, 204, as indicated by arrow 208, is resulting in contraction in diameter of device 200 and corresponding movement from right to left. Other configurations of strings can be used to tether an embolism protection device to facilitate removal and to contract the device, which may depend on the particular shape and structure of the device. Another embodiment of particular interest of an embolism protection device with a deployment tool that remains tethered to the device is described in detail in the following section.

Other embolism protection device configurations that can be adapted for fiber based devices are described in copending U.S. patent application Ser. No. 10/414,909 to Ogle, entitled "Embolism Protection Devices," incorporated herein by reference.

The embolism protection devices can comprise a composite of different structures, materials and/or bioactive agents. In particular, in these embodiments, the embolism protection device can have identifiable portions that are compositionally distinct with respect to the average composition within the portion. In some embodiments, the portions are positioned such that the flow or a substantial fraction of the flow passes sequentially through one section followed by another section. In such a configuration, generally at least about 25% of the flow volume and in other embodiments at least about 80% of the flow volume flow sequentially through the first portion followed by the second portion. A person of ordinary skill in the art will recognize that additional ranges of flow within the explicit ranges are contemplated and are within the present disclosure.

Figure 13:
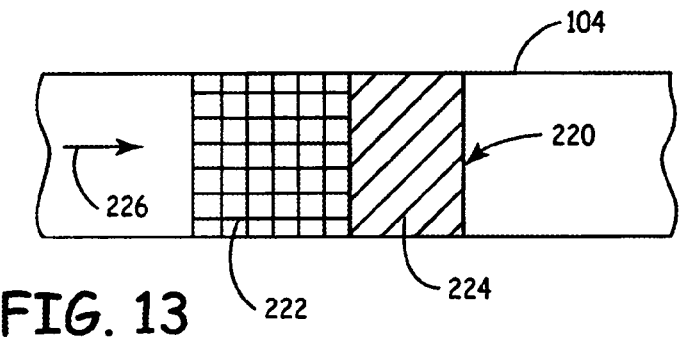
FIG. 13 is a schematic side view of an embolism protection device with two portions having different properties.

For example, as shown in FIG. 13, embolism protection device 220 comprises an up-flow portion 222 and a down-flow portion 224, where flow through the vessel is indicated with arrow 226. In some embodiments, up-flow portion 222 can elute, for example, a weak acid that tends to dissolve at least some emboli, while down-flow portion 224 can comprise a buffer that neutralizes the weak acid as it flows downstream. Up-flow portion 222 and/or down-flow portion 224 can comprise fibers, such as SCF fibers, as described herein.

In some embodiments, up-flow portion 222 and down-flow portion 224 can be separable. Thus, for example, up-flow portion 222 can provide a fiber mesh, a fiber bundle and/or another porous material across the flow to collect emboli for subsequent removal. Down-flow portion 224 can be a tubular structure that does not significantly alter the flow, but elutes a bioactive agent, such as tPA and/or NO. Since the portions separate, up-flow portion 222 can be taken from the vessel to remove the trapped emboli while down-flow portion remains in the vessel to elute beneficial agents. In alternative embodiments, the positions of the two portions can be reversed with respect to the flow and the portion to be removed, i.e., the down-stream portion can be removed to leave the up-stream portion. In variations on this embodiment, the down-flow portion can also trap emboli. Thus, following the removal of the up-flow portion, the down-flow portion can be effective to trap emboli. The down-flow portion can be formed from a bioresorbable material such that it dissolves at a desired rate.

The structures in FIGS. 1-13 are representative structures for the embolism protection device. Additional structures can be formed based on the disclosure herein.

In some embodiments, the embolism protection devices can be distributed along with other components that can be used along with other instruments that facilitate the use of the embolism protection device. For example, an embolism protection device can be distributed along with delivery tools, retraction devices, tools for the delivery of biologically active agents, instructions and other suitable tools. Suitable delivery tools include, for example, sheaths and/or cannula into which the embolism protection device can be placed for delivery along with other catheter components that can facilitate the delivery of the device. Suitable retraction devices that facilitate the removal of the embolism protection device are described herein, which can be distributed with the embolism protection device. For the delivery of a biologically active agent along with the embolism protection device, a guide wire with a hollow core and/or a cannulated syringe can be distributed with the embolism protection device. The cannulated syringe can be connected to the guide-wire for the delivery of a biologically active agent in the vicinity of the embolism protection device within the patient's vessel. The guide wire may or may not be associated with the embolism protection device as a tether. In addition, the embolism protection device can be distributed with instructions, which can take to form of written instructions and/or electronic copies, including, for example, a direction to a suitable web site. The commonly distributed elements can be distributed in one or more containers, for example, as a kit. While the embolism protection device generally is disposable following removal from the patient, the other individual elements distributed with the embolism protection device may or may not be reusable following sterilization.

Specific Integrated Systems

In some embodiments of interest, an embolism protection device comprising fibers is formed into an integrated structure that facilitates the delivery, deployment and recovery of the device. In particular, the devices are suitable for placement past an obstruction such that the embolism protection device can be deployed prior to the performance of a procedure on the obstruction. The integrated apparatus generally comprises a guidewire, a hypotube and the embolism protection device. Relative longitudinal motion of the hypotube over the guide wire can be used to deploy the embolism protection device. In some embodiments, the hypotube is dimensioned for the placement of a treatment structure over the hypotube for treatment of an obstruction.

Figure 14:
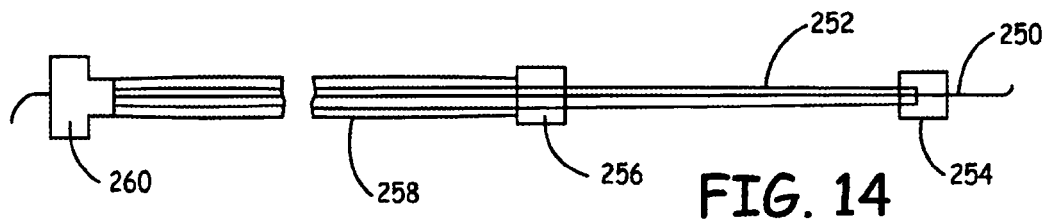
FIG. 14 is a side view of an integrated system with an embolism protection device integrated with a delivery system.

Referring to FIG. 14, the integrated device comprises a guidewire 250, a hypotube 252, an embolism protection device 254, a treatment structure 256, a catheter 258 and a hub/controller 260. Guidewire 250 fits within an inner lumen of hypotube 252. In embodiments of particular interest, hypotube 252 has an approximate outer diameter similar to that of a conventional guidewire. Then, conventional treatment structures can be delivered over the outside of the hypotube.

The length of hypotube 252 can generally be selected for the particular application. For example, for intervention in the aorta, the hypotube generally would have a length from about 190 cm (63 inches) to about 300 cm (106 inches). The cross section of the hypotube can be characterized by an inner diameter and an outer diameter. The inner diameter general ranges from about 0.001 inches to about 0.01 inches, in further embodiment from about 0.003 inches to about 0.008 inches and in additional embodiments from about 0.005 inches to about 0.007 inches. The outer diameter generally ranges from about 0.04 inches to about 0.009 inches, in further embodiments from about 0.03 inches to about 0.010 inches, in additional embodiments from about 0.02 to about 0.011 inches and in other embodiments from about 0.015 inches to about 0.013 inches, with standard guidewire outer diameters being about 0.014 inches. The guidewire has a diameter just slightly less than the inner diameter of the hypo tube by about 0.002 inches to about 0.003 inches. A person of ordinary skill in the art will recognize that additional ranges within the explicit ranges for the diameters are contemplated and are within the present disclosure.

In some embodiments, the guidewire has a length such that the guidewire extends past the distal end of the hypotube while extending also from the proximal end of the hypotube. Generally, the guidewire extends from the proximal end of the hypotube to provide for independent manipulation of the guidewire relative to the hypotube, especially for longitudinal movement and from the distal end for attachment to a medical device such as grippers or an embolism protection device. In general, it is desirable to be able to transfer torque from the hypotube to the guidewire to be able to rotate the tip of the guidewire with less fade of the rotational motion from the proximal end to the distal end of the guidewire. To accomplish this objective, it is possible to rotationally couple the hypotube without prohibiting the longitudinal motion of the hypotube relative to the guidewire. For example, the coupling can be accomplished with a key/keyway interaction, a coil that couples with the application of torque or a compression coupling. The torque coupling of the hypotube and the guidewire is described further in U.S. Provisional Patent application Ser. No. 60/550,880 to Pikorney et al., filed on Mar. 6, 2004, entitled "Steerable Guide Wire And Shaft With Small Diameters," incorporated herein by reference.

The embolism protection device can be any suitable device that can be deployed using the integrated structure. In particular, devices based on an expanding structure, such as hydrogels and/or shape memory fibers, as described in copending U.S. patent application Ser. No. 10/414,909 to Ogle, entitled "Embolism Protection Devices," incorporated herein by reference. Two embodiments of interest are described in further detail. In general, embolism protection devices employing fibers, such as SCF fibers, can be advantageously used with this integrated structure.

Figure 15:
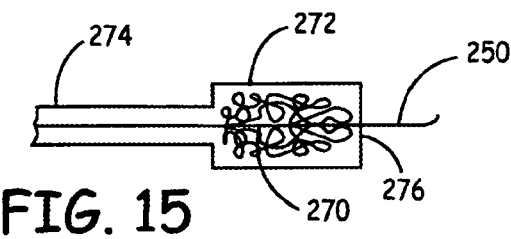
FIG. 15 is a fragmentary side view of an embodiment of an embolism protection device for use in the integrated system of FIG. 14.

Referring to FIG. 15, an embolism protection device 270 is shown within an optional expanded section 272 on a hypotube 274. Expanded section 272 has an opening 276 at the distal end of hypotube 274. If the embolism protection device has a small enough profile before deployment, the expanded section is not needed if the device can be covered with the hypotube alone. Embolism protection device 270 is attached to guidewire 250. The attachment of fibers to the guidewire can be accomplished with an adhesive, with chemical bonding and/or with mechanical entanglement. Embolism protection device 270 comprises an expanding polymer such that release of the device from the expanded section results in the deployment of the device within a vessel. The expanding polymer can be, for example, a fiber, such as an SCF fiber, that has shape memory upon heating to body temperature. The released fibers resume their memory shape at the expanded configuration to fill the vessel. Upon movement of hypotube 274 proximal to guidewire 250 (to the left relative to the guide wire as shown in FIG. 15), embolism protection device 270 exits hypotube 274 through opening 276 for deployment within the vessel.

Figure 16:
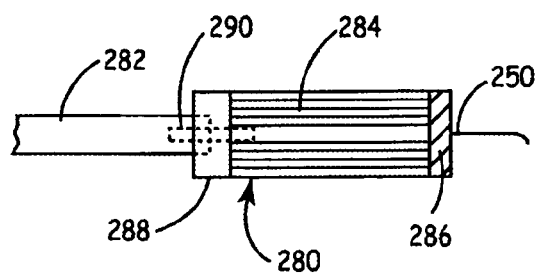
FIG. 16 is a fragmentary side view an alternative embodiment of an embolism protection device for use with the integrated system of FIG. 14.
Figure 20:
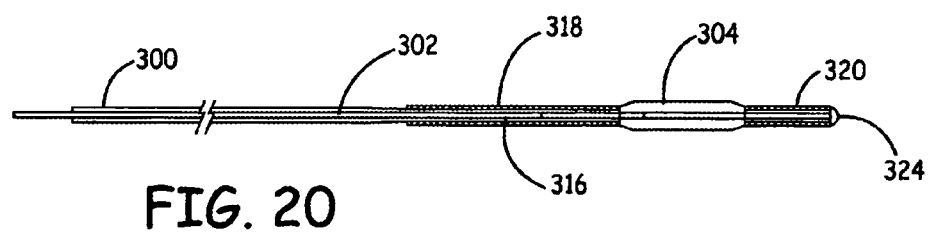
FIG. 20 is a sectional side view of a particular embodiment of an integrated embolism protection device and delivery tool.

Another embodiment is shown in FIG. 16. In this embodiment, embolism protection device 280 is located at the distal end of hypotube 282. Guidewire 250 extends from embolism protection device 280. Embolism protection device 280 comprises a bundle of fibers 284, a first attachment structure 286, a second attachment structure 288, and generally a wire passageway 290. Bundle of fibers 284 are collected in a generally cylindrical configuration for delivery into the vessel, as shown in FIG. 16. The number of fibers in the bundle generally depends on the desired degree of filtration as well as the thickness of the fibers. In general, the number of fibers can be range from at least 10 fibers, in further embodiments from 25 fibers to 1,000,000 fibers, in other embodiments from 50 fibers to 10,000 fibers and in additional embodiments, from 100 fibers to 5,000 fibers. The length of the fibers can be selected based on the size of the corresponding vessel. When deployed, the centers of the fibers are projected across the lumen of the vessel. Thus, the unconstrained length of the fibers between attachment structures 286, 288 should be at least double the radius of the vessel. In some embodiments relating to the use of a plurality of fibers to expand within the lumen of a patient's vessel, it is generally appropriate to use fibers that have a length from about 2.2 to about 10 times the vessel radius, in some embodiments from about 2.4 to about 5 times the vessel radius and in further embodiments from about 2.6 to about 4 times the vessel radius. For placement in a human vessel, the fibers generally have a length from about 0.5 mm to about 100 mm, in other embodiments from about 1 mm to about 25 mm, and in further embodiments from about 2 mm to about 15 mm. A person of ordinary skill in the art will recognize that additional ranges of fiber numbers and fiber length within the explicit ranges are contemplated and are within the present disclosure. In one specific embodiment, the device comprises 480-6 denier SCF fibers in a bundle and a crossing profile of 0.033 inches (2.5 French).

First attachment structure 286 attaches fibers 284 to guidewire 250. Thus, the distal end of the fibers is attached to the guidewire. Similarly, second attachment structure 288 secures the proximal end of the fibers to hypotube 282. Wire passageway 290 is a tube that extends through the second attachment structure 288 to provide a conduit past the second attachment structure. Guidewire 250 passes through wire passageway 290 such that guidewire 250 is able to move longitudinally relative to second attachment structure 288 and therefore to hypotube 282. Attachment at the first attachment structure and the second attachment structure can independently be achieved, for example, with a suitable adhesive (some of which are described below), with a band that is tightly applied over the fiber bundle and/or with heat bonding of the fibers, although other suitable attachment approaches can be used. Wire passageway 290 can be formed from a suitable biocompatible materials that has sufficient mechanical strength to avoid collapsing onto guidewire 250 when sufficient force is applied to hold fibers 284 in place.

Following deployment, the center of fibers 284 project outward from guidewire 250, as shown in FIG. 17. An end view is shown schematically in FIG. 18. Thus, fibers 284 fill the lumen of the vessel to filter the flow without blocking desirable flow. The deployment process is shown in FIG. 19 A-C. In FIG. 19A, an outer sheath 292 covers device 280 and hypotube 282 during delivery. A marker 294 on hypotube 282 provides a reference point. As shown in FIG. 19B, sheath 292 is withdrawn to expose device 280. Sheath 292 can be completely removed. As shown in FIG. 19C, pulling guidewire 250 proximal relative to hypotube 282 deploys embolism protection device 280.

Referring to FIG. 14, therapy device 256 can be any suitable device to treat the patient within the vessel. For example, therapy device 256 can be a balloon, a stent, or the like. Catheter 258 can be any suitable catheter, such as a guide catheter for the delivery and actuation of therapy device 256. Suitable devices are well know in the art, for example, as described further in U.S. Pat. No. 6,464,718 to Miller et al., entitled "Balloon Catheter For Stent Delivery Having Microchannels And Method," and U.S. Pat. No. 6,491,617 to Ogle et al., entitled "Medical Devices That Resist Restenosis," both of which are incorporated herein by reference. These devices can be delivered using hypotube 252 as an effective guidewire to guide and facilitate their delivery.

Hub/controller 260 can be used to mediate introduction of the devices into the patient's vessel without the undesirable loss of fluids. Hub/controller 260 generally forms a seal at the patient's skin to prevent fluid loss. Access ports provide for introduction and manipulation of the tools within the vessel. Hub/controller may or may not include a handle or the like. Generally, guidewire 250 extends from hub 260 to provide for the relative motion of guidewire 250 and hypotube 252, although guidewire 250 can be connected to a trigger or other actuator to control its relative position relative to hypotube 252. Suitable hubs and similar catheter control devices are known in the art, for example, as described in U.S. Pat. No. 5,906,619 to Olson et al., entitled "Disposable Delivery Device For Endoluminal Prosthesis," incorporated herein by reference.

Figure 21:
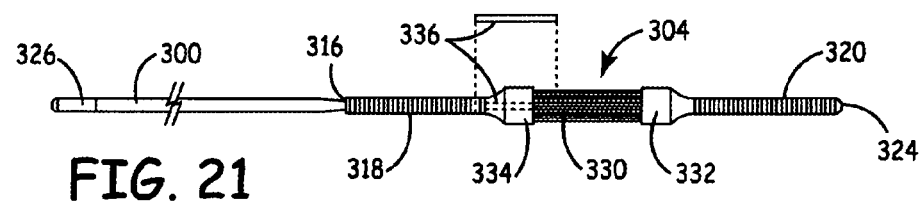
FIG. 21 is a side view of the integrated device of FIG. 20.
Figure 22:
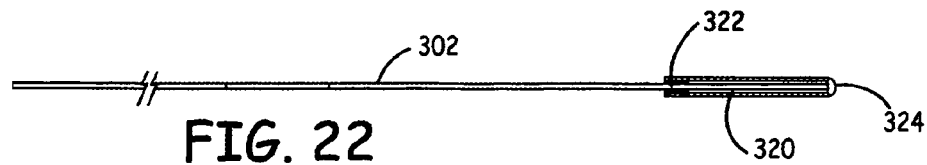
FIG. 22 is a side view of the guidewire of the integrated device of FIG. 20.
Figure 23:
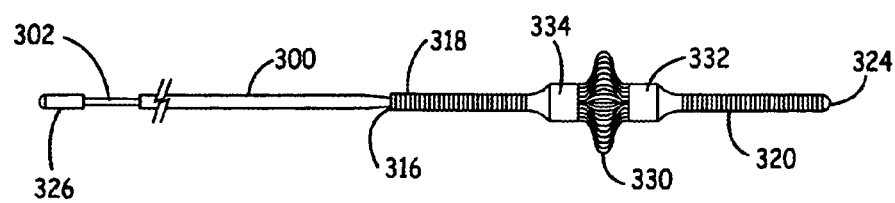
FIG. 23 is a side view of the device of FIG. 20 following expansion of the embolism protection device.
Figure 24:
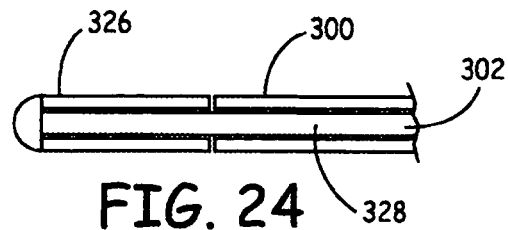
FIG. 24 is a fragmentary, expanded view of the proximal tip of the device of FIG. 20 with a kink in the guidewire.
Figure 25:
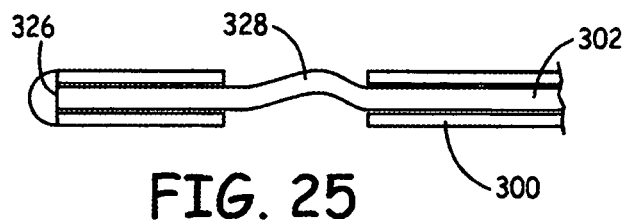
FIG. 25 is a fragmentary expanded view of the proximal tip of the device of FIG. 24 with a pulled guide wire.
Figure 26:
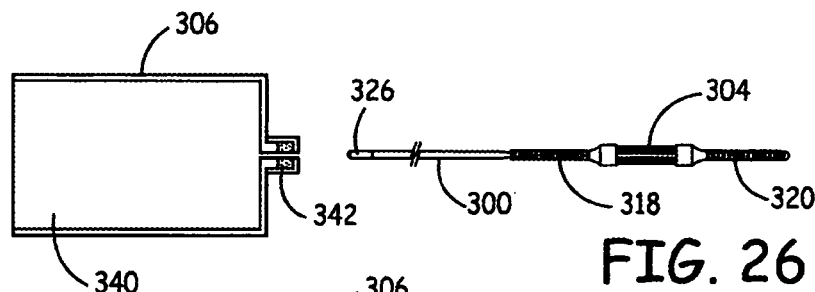
FIG. 26 is a side view of the device of FIG. 20 with an associated hand guard positioned for attachment.

One specific embodiment is shown in FIGS. 20-29. In this embodiment, the integrated instrument comprises a hypotube 300, a guidewire 302, an embolism protection device 304 and a hand guard 306. Referring to the sectional view in FIG. 20 and the side view in FIG. 21, hypotube 300 has a tapered section 316 at its distal end that mimics the taper on a conventional guidewire. A wire coil 318 is located over the tapered section 316. Guidewire 302 is covered with a coil 320 at its distal end, as shown in FIG. 22. Coil 320 is connected with solder 322 and a weld 324, although other attachment approaches can be used. Grip 326 is attached to the proximal end of guidewire 302. Furthermore, guidewire 302 can have a kink 328 near grip 326, as shown in FIGS. 24 and 25. Kink 328 can help hold hypotube 300 and guidewire 302 in a configuration with the embolism protection device not deployed for delivery. Hypotube 300, guidewire 302, wire coil 318, coil 320 and grip 326 can all be formed from stainless steel, although other suitable materials can be used.

In this embodiment, embolism protection device 304 comprises a bundle of SCF fibers 330 attached at first attachment 332 and second attachment 334, as shown in FIGS. 21 and 23. A 0.1 inch long tube 336, which can be formed from polyimide polymer, is located within the second attachment 334 with guidewire 302 extending within the tube. The fibers are swaged/crimped at the two attachments 332, 334 to a diameter of 0.033 inches with radiopaque bands. After crimping, the fiber bundles are bonded at each end with an adhesive, such as cyanoacrylate.

Figure 27:
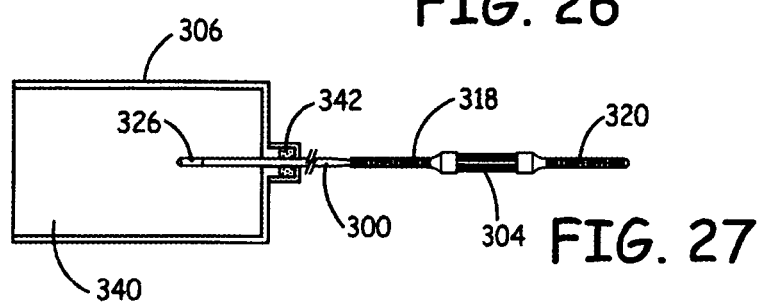
FIG. 27 is a side view of the hand guard of FIG. 26 connected to the device of FIG. 20.
Figure 28:
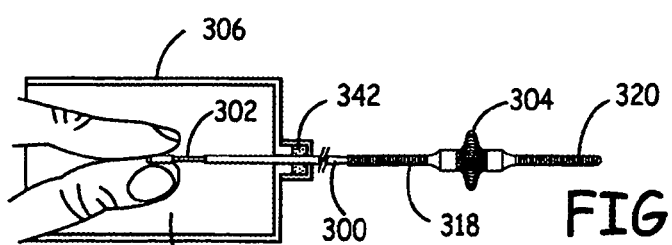
FIG. 28 is a side view depicting the pulling of the guide wire within the hand guard of FIG. 27.
Figure 29:
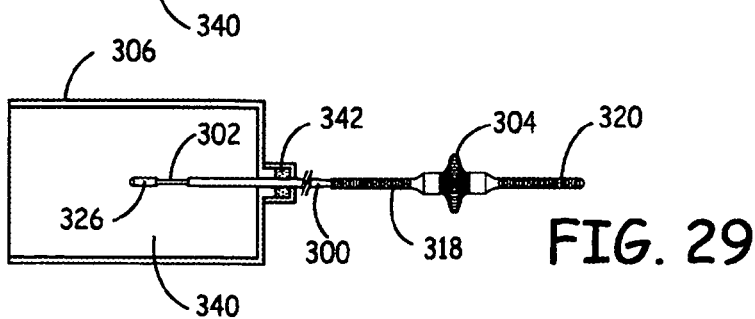
FIG. 29 is a side view of the device attached to the hand guard as shown in FIG. 27 with the pull wire extended.

Hand guard 306 is shown in FIGS. 26-29. Hand guard 306 comprises a guard chamber 340 and a connection 342. Connection 342 can be a Touhy Borst connection for securing the hypotube 300, as shown in FIG. 27. Touhy Borst connections are described further in U.S. Pat. No. 5,795,307 to Krueger, entitled "Shunt Tap Apparatus And Method," incorporated herein by reference. A health care professional can reach within guard chamber 340 to pull guidewire 302 to deploy embolism protection device 304, as shown in FIG. 28. Guard chamber 340 protects the exposed pull wire from accidental bending. If the hypotube is to be retracted into a percutaneous transluminal coronary angeoplasty (PTCA) catheter, hand guard 306 can easily be removed.

Materials

In general, the materials that contact the patient's bodily fluids and tissues are biocompatible. Biocompatible materials generally are non-toxic, non-carcinogenic and blood compatible and do not induce hemolysis or a significant immunological response. In general, the devices described herein can comprises various materials for the particular components. In particular, we consider the composition of fibers for incorporation into an embolism protection device. The discussion of SCF fibers is covered in the following headed section. Suitable additional materials can be, for example, polymers, metals, ceramics, bioactive compounds, and the like. Bioactive compounds are described further below.

Any non-biocompatible materials can be used for portions of the apparatus that do not contact bodily fluids. Non-biocompatible components can be used for manipulating and/or structurally supporting the other portions of the device that do contact bodily fluids. For example, various materials, such as conventional structural materials, can be used to form the structural and control portions of a catheter apparatus that remain outside of the body, such as the hand guard of FIGS. 26-29. Similarly, various control apparatus can be used for manipulating a catheter or the like in conjunction with certain percutaneous appartuses. Catheter apparatuses are described further, for example, in U.S. Pat. No. 6,176,843 to DiCaprio et al., entitled "Catheter With Distal Manifold Prep Valve/Manifold," incorporated herein by reference.

With respect to suitable biocompatible materials appropriate ceramics include, without limitation, hydroxyapatite, alumina and pyrolytic carbon. Biocompatible metals include, for example, titanium, cobalt, stainless steel, nickel, iron alloys, cobalt alloys, such as Elgiloy®, a cobalt-chromium-nickel alloy, MP35N, a nickel-cobalt-chromium-molybdenum alloy, and Nitinol®, a nickel-titanium alloy. Additional materials, such as metals, can be introduced into a polymer component to render the portion of the device radio-opaque such that it can be visualized via angiography or clinical techniques. Generally, suitable metals comprise biocompatible metals. Guide wires, tethers and the like can also be formed from these biocompatible metals and/or biocompatible polymers, which can be formed from the same materials as the biocompatible fabrics described below.

Also, the embolism protection device can further comprise a biocompatible adhesive, such as for forming the device and/or applying a coating. In some embodiments, a medical adhesive can be combined with a bioactive agent and placed within the surface capillaries to deliver the bioactive agent with selected delivery based on the character of the adhesive, which can be a resorbable adhesive. For convenience, adhesive, as used herein, refer generally to the adhesive in a form for application as well as the adhesive composition following curing in a set form. Appropriate medical adhesives should be biocompatible, in that they are non-toxic, non-carcinogenic and do not induce hemolysis or an immunological response. In general, the adhesive can be a single component adhesive or multi-component adhesive. Further suitable adhesives include synthetic adhesives, natural adhesives and combinations thereof. For example, suitable biocompatible adhesives include commercially available surgical adhesives, such as one component cyanoacralate adhesives (such as 2-octyl cyanoacrylate, Dermabond™, from Ethicon Products), fibrin glue (such as Tissucol® from Baxter) and mixtures thereof.

Suitable two-component synthetic adhesives include, for example, urethane-based polymers, copolymers, and mixtures thereof. Polyurethanes are ester-amide derivatives of carboxylic acids. Urethane oligomers/prepolymers can be formed with terminal reactive functional groups. Because of the terminal functional groups, the prepolymers are particularly suitable for the formation of crosslinked mixed polymers exhibiting a range of desirable properties generally characteristic of polyurethanes and of the other components. With respect to the formation of an adhesive, in certain embodiments, the urethane prepolymer can be used as one component of the adhesive, with a crosslinking agent or agents being the other component or components of the adhesive. Isocyanate (—NCO)-terminated urethane prepolymers are particularly suitable adhesive components. Polyurethanes including polyurethane prepolymers (urethane oligomers) can be formed either by the reaction of bischloroformates with diamines or the reaction of diisocyanates with polyhydroxy compounds. Urethane based medical adhesives are discussed further in published PCT application WO00/43050, entitled "Medical Adhesives," incorporated herein by reference.

Adhesives based on components that are natural compositions generally are based on inherent natural binding affinities and corresponding biological responses. Generally, one or more components of the adhesive are a protein or protein based compound. Protein is intended to be interpreted broadly in terms of any compound with a polypeptide (i.e., poly amino acids) component, and may include derivatives of natural proteins and polypeptides with additional covalently or non-covalently attached components, such as additional polypeptides, nucleotides, carbohydrates, and other organic or inorganic compounds. Protein components generally contain amino acids with side chains with functional groups useful for binding with the remaining adhesive components. Also, if the substrate is a crosslinked tissue, an adhesive component can replace functional groups that had been eliminated in the tissue substrate by reactions during the crosslinking process.

A type of biological adhesive is based on the protein fibrinogen. Fibrinogen, also known as factor I, is involved in natural blood clotting processes The protein thrombin removes one or two peptides from fibrinogen to form fibrin. Thrombin is also involved in the blood clotting process. A variety of fibrin adhesives have been based on the crosslinking of fibrin. Fibrin glues generally involve combinations of fibrinogen, thrombin and Factor XIII. Factor XIII also is involved in the natural wound healing mechanism. Factor XIII, also known as fibrin stabilizing factor, is activated by thrombin, and converts soluble fibrin to an insoluble clot. Fibrin adhesives polymerize and also covalently crosslink with collagen and other tissue components to form a liquid tight bond. The final amounts of the fibrinogen, thrombin or factor XIII components in the complete adhesive can be adjusted, as desired, to yield selected adhesive properties, such as strength and/or cure times, or for convenient application.

U.S. Pat. No. 4,818,291 to Iwatsuki et al., incorporated herein by reference, describes the inclusion of silk-fibroin protein into a fibrin glue to enhance its mechanical strength. Fibrin adhesives may also contain albumin, as described in U.S. Pat. No. 4,414,976 to Schwarz et al., incorporated herein by reference.

Another type of adhesive includes a biological component and a synthetic component. Generally, the biological component includes a protein. For example, gelatin-resorcinol aldehyde adhesives involve a gelatin-resorcinol material that is formed by heating gelatin and resorcinol. Gelatin is formed by hydrolytic activity on collagen protein. Formaldehyde, glutaraldehyde or the like can be used to crosslink the gelatin-resorcinol material to complete the formation of the glue. Such adhesives are described further in U.S. Pat. No. 5,385,606 to Kowanko, incorporated herein by reference. Similar adhesives based on proteinaceous material have been described in U.S. Pat. No. 5,583,114 to Barrows et al., incorporated herein by reference.

The adhesives can contain additives to modify the mechanical properties of the adhesive. Suitable additives include, for example, fillers, softening agents and stabilizers.

The use of adhesives to facilitate and control the delivery of bioactive agents from a SCF fiber is described further in copending U.S. patent application Ser. No. 10/781,503 to Ogle et al., filed on Feb. 18, 2004, entitled "Medical Article Incorporating Surface Capillary Fiber," incorporated herein by reference.

As noted above, components of the medical device can be formed from polymers. The character of the appropriate polymers generally depends on the particular use of the component. In some embodiments, the polymers are elastic or flexible polymers, while in other embodiments the polymers are rigid polymers that can be used to form structural components. In general, for components that do not contact bodily fluids and polymers with desired properties can be used, such as commercially available polymer. For components that contact bodily fluids a variety of biocompatible polymers can be adapted for use. Suitable flexible polymers include, for example, polyesters, such as polyethylene teraphthalate, polyurethanes, polydimethyl siloxane, polytetrafluoroethylene and copolymes and mixtures thereof. Suitable rigid polymers include, for example, polyacetals, such as Delrin® and Celcon®, polysulfones, polyethersulfones, polyarylsulfones, polyetherether-ketones, polyetherimides and copolymers and mixtures thereof. Radio-opaque polymers include, iodinated and bominated polymers, as described, for example, in U.S. Pat. No. 6,475,477 to Kohn et al., entitled "Radio-Opaque Polymer Biomaterials," incorporated herein by reference.

In some embodiments, it is desirable to use a resorbable polymer, such as, polysaccharides, e.g., polydextran, cellulose and starch, hydroxyethyl starch, derivatives of gelatine, polyvinylpyrrolidone, polyvinyl alcohol, poly[N-(2-hydroxylpropyl) methacrylamide], polyglycols, polyesters, poly(orthoesters), poly(ester amides), polyanhydrides and copolymers and mixtures thereof. Resorbable polyesters include, for example, poly(hydroxy acids) and copolymers thereof, poly(epsilon-caprolactone), poly (dimethyl glycolic acid), poly (hydroxy butyrate) and copolymers and mixtures thereof. Other resorbable polymers include, for example, D, L-polylactic acid, L-polylactic acid, poly(glycolic acid), and copolymers of L-lactic acid, D-lactic acid and glycolic acid.

Also, portions of the device, such as portions that contact a patient's bodily fluids, can be covered with a biocompatible fabric. Biocompatible fabrics can be formed from a variety of biocompatible materials, such as silk, nylon and/or polyesters, including, for example, Dacron® polyester. The fabric may or may not be formed from the SCF fibers, such as by weaving. Furthermore, the fabric may or may not be woven. The fabric can be selected to have an appropriate porosity for the desired use of the material. For example, if the fabric is formed from SCF fibers, the pore sizes can be selected to provide for flow around the fibers. For nonwoven fabrics, a desired porosity can be introduced by mechanically puncturing the fabric with a fine needle or the like or by laser drilling appropriate pores. A wide variety of lasers with moderate power can be used for the drilling and conventional optics can be used to focus the laser beam to produce the desired pore size.

In some embodiments, the embolism protection device can comprise a biodegradable shape adjusting or memory polymer. These polymers can transition to a memory shape upon application of a stimulus, such as a temperature change. In particular, biodegradable polymers are available that resume a memory shape upon placement at body temperature or pH. The memory shape can be an expanded form that would extend the device across the lumen of the vessel. Thus, the memory polymer can expand the embolism protection device without the assistance of a swelling polymer, although the device may or may not comprise a blend or copolymer with the memory polymer and a hydrogel or other swelling polymer. Suitable memory polymers are described further in U.S. Pat. No. 6,160,084 to Langer et al., entitled "Biodegradable Shape Memory Polymers," incorporated herein by reference. In some embodiments, the device with a biodegradable polymer can be combined with an initial amount of tPA and vectors to deliver an expressible tPA gene to transfect nearby cell to supply tPA on a longer term basis after the initial tPA with the device has eluted. The degradation of the device avoids the need to eventually remove the device and the supplies of tPA dissolve emboli such that the device does not become clogged with emboli during a more extensive implantation.

In some embodiments, block copolymers can be used to introduce a stable form of a polymer blend, such as a hydrogel that is bonded to a structural polymer. In particular, the hydrogel can be grafted onto the structural polymer material based on knowledge in the art. In particular, polymeric materials have been grafted together using plasma, although other crosslinking approaches can similarly be used. A high-energy plasma technique generates active groups in the polymer, which facilitate the grafting of the second substrate to the first. The chemical composition of the two materials is complementary to this potential bonding and has been individually used to generate graft copolymers. (24) This copolymer matrix has the potential to swell and develop significant porosity in a controllable fashion. This reaction results in the grafting of polyacrylamide onto the (PET) fibers. This grafting can be further or alternatively facilitated with ultraviolet crosslinking. (25) (See Equation 1.)

Reaction of polyacrylamide and PET polyester

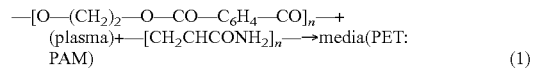

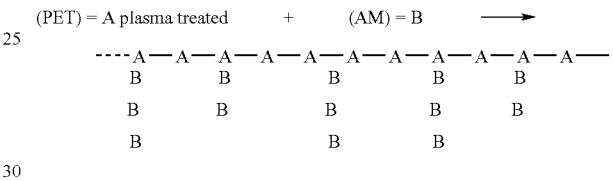

The polymer components can be prepared by any of a variety of approaches including, for example, conventional polymer processing methods. Various molding techniques can be used, such as injection molding, casting, compression molding and the like. However, other polymer processing approaches can similarly be used, such as extrusion, calendering, blowing and the like. Suitable approaches include, for example, injection molding, which is suitable for the production of polymer components with significant structural features, and rapid prototyping approaches, such as reaction injection molding and stereo-lithography. SCF fibers are described in more detail below, although other fibers can similarly be used such as other fibers formed with biocompatible materials, such as the biocompatible polymers described above.

Other embodiments could employ surfactants or other surface finishes, as constituents for the medical device, which can modulate fluid management or biological rejection to the device. Also, other embodiments may entail modulation of these coatings to produce either a hydrophilic or hydrophobic nature to the materials.

SCF Fibers

As used herein, SCF fibers refer broadly to fibers having channels or capillaries along the surface running generally along the length of the fiber or a portion thereof. Fibers have their usual meaning as structures with a length that is significantly larger than the dimensions along a cross section perpendicular to the length. The capillaries can run along substantially the entire length or a fraction thereof. Due to the presence of the capillaries, a cross section through the fiber at the capillary(ies) has a shape with an edge having changing curvatures. A suitable cross sectional shape is shown schematically in FIG. 1, although any of wide range of cross sectional shapes are suitable as long as a surface capillary is formed. As shown schematically in FIG. 1, the fiber has eight surface capillaries. For comparison, a fiber without surface capillaries is shown schematically in FIG. 2 at the same magnification as the fiber in FIG. 1 having roughly the same surface area as the fiber in FIG. 1.

SCF fibers for use in the medical devices are generally formed from biocompatible polymers. SCF fibers can be fabricated from synthetic polymers as well as purified biological polymers and combinations thereof. Suitable synthetic polymers include, for example, polyamides (e.g., nylon), polyesters (e.g., polyethylene teraphthalate), polyacetals/polyketals, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. Based on desirable properties and experience in the medical device field, suitable synthetic polymers include, in particular, polyether ether ketones, polyacetals, polyamides (e.g., nylons), polyurethanes, polytetrafluoroethylene, polyester teraphthalate, polycarbonates, polysulfone and copolymers and mixtures thereof.

Bioresorbable synthetic polymers can also be used such as dextran, hydroxyethyl starch, derivatives of gelatin, polyvinylpyrrolidone, polyvinyl alcohol, poly[N-(2-hydroxypropyl) methacrylamide], poly(hydroxy acids), poly(epsilon-caprolactone), polylactic acid, polyglycolic acid, poly(dimethyl glycolic acid), poly(hydroxy butyrate), and similar copolymers. Based on experience in the medical field, suitable resorbable polymers include, in particular, polylactic acid, polyglycolic acid, and copolymers and mixtures thereof.

Appropriate polymers also include biological polymers. Biological polymers can be naturally occurring or produced in vitro by fermentation and the like. Suitable biological polymers include, without limitation, collagen, elastin, silk, keratin, gelatin, polyamino acids, cat gut sutures, polysaccharides (e.g., cellulose and starch) and mixtures thereof. Biological polymers generally are bioresorbable. Purified biological polymers can be appropriately formed into a polymer material for further processing into fibers.

A suitable length of the fibers generally depends on the specific use of the fiber. In a broad sense, the fibers generally range in size from about 500 microns to about 10 centimeters in length, although lengths outside this range are also contemplated. Also, in general, fibers have a large aspect ratio, which is the ratio of the length of the fiber to its width, with a value typically of at least about 3. Aspect ratios can be at least about 10 in some embodiments, in further embodiments at least about 100, in other embodiments at least about 1000, and in additional embodiments from about 2000 to about 10,000. Similarly, the capillaries generally have a length along the fiber length that is at least a factor of three greater than the width of the capillary. In some embodiments, the surface capillaries extend along at least about 5 percent of the fiber length, in further embodiments at least about 20 percent, in further embodiments at least about 40 percent and in other embodiments at least about 60 percent. In some embodiments, the surface capillaries extend substantially along the entire length of the fiber. A person of ordinary skill in the art will recognize that additional ranges of fiber length, aspect ratio and capillary channel extent are contemplated and are within the present disclosure. In particular, one or both ends of the fiber may have different properties or no surface capillaries in some embodiments.

The properties of the surface channels and the corresponding cross-section of the fiber generally depends on the process used to form the fibers. U.S. Pat. No. 4,842,792 to Bagrodia et al., entitled "Drafting Process For Preparing A Modified Polyester Fiber," incorporated herein by reference, describes one approach for forming a fiber with a continuous surface "groove" that runs along the length of the fiber. The process in the '792 patent forms the groove starting from a conventional fiber. Another form of shaped fibers is described in U.S. Pat. No. 5,277,976 to Hogle et al., entitled "Oriented Profile Fibers," incorporated herein by reference. Other shaped fibers notches or channels are described in U.S. Pat. No. 5,458,963 to Meirowitz et al., entitled "Nonwoven Web Containing Shaped Fibers," incorporated herein by reference. Fiber with fairly complex surface channel geometry are described in U.S. Pat. No. 5,972,505 to Phillips et al., entitled "Fibers Capable Of Spontaneously Transporting Fluids," incorporated herein by reference. A further approach for forming a fiber with surface capillaries is described in U.S. Pat. No. 5,200,248 to Thompson et al. (hereinafter the '248 patent), entitled "Open Capillary Channel Structures, Improved Process For Making Capillary Channel Structures, And Extrusion Die For Use Therein," incorporated herein by reference. The Background section of the '248 patent additionally references a variety of alternative embodiments of approaches for forming fibers with surface channels or capillaries. Any of these approaches can be used. However, the fibers formed by the process of the '248 patent itself have desirable characteristics and versatility.

In some embodiments, the SCF fibers can also have shape memory. These fibers can be heated gently to cause the fibers to curl. The curled fibers can be stretched straight at room temperature. Upon heating to body temperature, the fibers resume the curled configuration. By using a bundle of the stretched fibers, the individual fibers of the bundle curl upon delivery due to body heat/hydration to form a fibrous filter mat that can entrap emboli within the fibrous network.

Since suitable fibers can be formed in a variety of ways, the cross sectional properties of the fibers can have similar variety. In general, the cross sectional properties of the fibers are relatively uniform along the length of the capillaries, although such a property is not needed in some embodiment for desirable function. The cross sectional properties can be considered as an average of the cross section along the length of the fiber with the surface capillaries. Due to the presence of at least one surface capillary, the outer contour of the cross section has at least one change in curvature. In some embodiments, the fiber has a plurality of surface capillaries with corresponding changes in curvature. Thus, a fiber can have a single surface capillary, two surface capillaries, or at least three surface capillaries, such as in appropriate embodiments from 3-25 surface capillaries as well as any and all values and subranges within this range. For example, the cross section has an outer perimeter that is formed by tracing along the outer surface of the cross section.

The cross section can be characterized by a circumference that can be determined by magnifying the cross section, conceptually wrapping a tight string around the circumference, measuring the length of the conceptual string and scaling the length back according to the inverse of the magnification to obtain the circumference. Similarly, the area mapped out with this virtual string also characterizes the cross section of the fiber. The radius of the fiber can be estimated from the circumference if an overall circular shape is assumed since the circumference, c, can be related roughly to a radius, r, by the formula $c=2\pi r$. The capillaries themselves can be characterized roughly by their number, shape and wall thickness between the capillaries. Suitable wall thickness can depend on the size of the capillaries as well as the overall thickness of the fiber.

As with the fiber length, the thickness of the fibers can be selected appropriately for the particular use of the fiber. Fiber thickness can be measures in several ways. As described in the previous paragraph, the radius of the fiber can be roughly estimated from the assumption of a circular cross section. Alternatively, one can define an average diameter by taking an average cross section and then averaging the length of segments through the center of the cross section that intersect the circumference of the cross section. Also, calipers can be used to measure thickness, which can be averaged to obtain a value of the diameter. These various approaches at estimating the radius or diameter generally give values of roughly the same magnitude. Also, in the fiber field, a pragmatic way has been developed to characterize fiber thickness without the need to resort to magnification of the fibers. Thus, fiber thickness can be measured in units of denier. Deniers correspond to the number of grams per 9,000 meters of yarn with a larger value corresponding to a thicker fiber. In some embodiments, suitable fibers have diameters from 50 microns to about 5 millimeter, in further embodiments from about 100 microns to about 2 millimeters, and in additional embodiments from about 150 microns to about 1 millimeter. As measured in denier, SCF fibers can have sizes ranging from about 0.1 denier to about 1000 denier in size, in additional embodiments from about 0.5 denier to about 250 denier, in some embodiments from about 1.0 denier to about 200 denier, in other embodiments from about 2.0 denier to about 100 denier and in further embodiments from about 3.0 denier to about 50 denier. A person of ordinary skill in the art will recognize that additional ranges of fiber thickness in diameter measurements or in denier are contemplated and are within the present disclosure.

A capillary channel can have a width suitable for the particular application based on its function and its interaction with associated fluids. For many applications of interest, suitable capillary widths range from about 1 micron to about 0.5 mm (500 microns), in other embodiments from about 5 microns to about 250 microns, in further embodiments from about 10 microns to about 200 microns and in additional embodiments from about 25 microns to about 100 microns as well as all ranges and subranges within these. The width of a capillary channel can be evaluated from a measurement on a micrograph of fiber cross section based on the magnification. The width can be taken as the distance between the edges of the capillary along the circumference of the fiber such that the width corresponds with the surface opening of the capillary. A person of ordinary skill in the art will recognize that additional ranges of values of capillary widths within the explicit ranges are contemplated and are within the present disclosure.

Further characterization of the fibers can barrow from the approaches outlined in the '248 patent. In particular, the overall capillary sizes can be characterized. In some embodiments of interest, the fibers have a specific capillary volume of at least about 0.5 cc/g, in other embodiments at least about 1.0 cc/g, in further embodiments at least about 2.0 cc/g and in additional embodiments at least about 3.0 cc/g. Also, the specific capillary surface area can be at least about 500 $cm^2/g$, in some embodiments at least about 1000 $cm^2/g$, in further embodiments at least about 2000 $cm^2/g$, and in other embodiments at least about 3000 $cm^2/g$. A person of ordinary skill in the art will recognize that additional ranges of capillary volumes and capillary surface areas are contemplated and are within the present disclosure. Tests for evaluating these values are summarized below.

In some embodiments, it is desirable for aqueous liquid, such as bodily fluids or components thereof to enter the capillaries. For these embodiments, the polymer properties and the capillary properties can be selected appropriately such that the capillaries can accept the liquid accounting for the surface tension of the liquid and the chemical properties of the liquid and the fiber. In particular, it can be desirable to provide for aqueous liquid entry into the capillaries for embodiments involving removal of particulates from a bodily fluid and for embodiments involving transport of biological liquids through the channels. Thus, relatively hydrophilic polymers, such as polyesters, generally are suitable fiber materials for incorporating aqueous liquids into the capillaries.

While various capillary structures are covered herein, in some embodiments with high capillary volumes, the capillary walls can be particularly thin. If the capillary walls are thin, the capillary can collapse under compressive forces unless the polymer is resistant to compressive strain. Thus, in some embodiments, it is desirable for the polymers to have a modulus of elasticity of at least about 100 MPa and in other embodiments at least about 750 MPa at biological temperatures from about 35° C. to about 40° C. Similarly, the wetting properties of the polymer can be relevant. In some embodiments, the polymer has an adhesion tension with distilled water of at least about 20 dynes/cm and in further embodiments at least about 25 dynes/cm. With respect to the resulting capillary properties, the capillary structures in some embodiments exhibit a capillary sorption of at least about 1.5 cc/g at 5.0 cm capillary suction/hydrostatic tension with distilled water, in other embodiments at least about 4 cc/g at 5.0 cm and in further embodiments at least about 4 cc/g at 10 cm capillary suction. The test for capillary sorption is described below. A person of ordinary skill in the art will recognize that additional ranges of modulus of elasticity, adhesion tension, and capillary sorption within the explicit ranges are contemplated and are within the present disclosure.

Test methods for evaluating the specific capillary volume, the specific surface capillary area and the adhesion tension are described in detail in the '248 patent, which is incorporated herein by reference for the explicit description of the determination of these values.

In general, the fibers can be attached together for incorporating into a device. For example, the fibers can be attached using chemical crosslinking, adhesives, twisting, weaving, heat bonding, or the like or combinations thereof. Chemical crosslinking can involve the use of radiation or the like to active the polymer to form chemical crosslinks and/or crosslinking agents that can bond with two or more polymer fiber elements. Suitable adhesives for bonding the fibers or a portion thereof are described in detail below. The fibers can be twisted or braided, for example using conventional approaches, to form weaving or similar physical association can be used to form structures for use in the device. In general, if formed from appropriate polymers, fibers or portions thereof can be associated together using heat bonding, which can be controlled to form desired fusing without inducing an undesirable loss of the fiber and surface channel structure. Furthermore, the fibers can be associated with additional materials or the like within the device to secure the fibers and or form the device, as described further below.

Bioactive Agents

The medical devices or components thereof generally provide mechanical and structural functions within the patient. However, it may be desirable to combine the mechanical features of the device with biologically active agents to provide another dimension to the treatment.

In some embodiments the association of bioactive agents with the device can provide treatment to shrink or eliminate emboli, such as within an embolic protection device, and/or to deliver a bioactive agent in the vicinity of and/or downstream from the device. Suitable bioactive agents include, for example, thrombolytic (anti-thrombogenic) agents, anti-platelet agents, anti-coagulation agents, anitmicrobial agents, vascular-dilators, pro-coagulation agents, restenosis inhibitors, acidic agents, growth factors and combinations thereof.

Suitable thrombolytic agents include, for example, tissue-type plasminogen activator (tPA), mutated forms of tPA, such as TNK-tPA and YM866, urokinase, streptokinase, staphylokinase, and the like. In particular, tPA is a polypeptide that acts upon plasminogen to form plasmin. Plasmin breaks down fibrin, one of the main structural proteins in blood clots. (22,23) Plasmin also lyses fibrinogen, a precursor of fibrin. tPA can be produced according to the method described in U.S. Pat. No. 4,935,368 to Ryotaro et al., entitled "Process For Producing Tissue Plasminogen Activator," incorporated herein by reference. An effective precursor of tPA is described in U.S. Pat. No. 6,001,355 to Dowdle, entitled "Pro-tPA For The Treatment Of Thrombosis, Embolism And Related Conditions," incorporated herein by reference. Analogs, e.g. mutated forms, of tPA are known, for example, as are described in U.S. Pat. No. 5,106,741 to Marotti et al., entitled "Tissue Plasminogen Activator (TPA) Analogs," PCT published application WO 93/20194 to Sato et al., entitled "TPA Analog," and PCT published application WO 02/22832 to Xia et al., entitled "A Cell Line Expressing Mutated Human Tissue-Type Plasminogen Activator, The Constructing Strategy Thereof And Methods Of Preparing Expressed Protein," all three of which are incorporated herein by reference. Elsewhere in this application including the claims, tPA refers to natural tPA, fragments thereof and analogs thereof that are effective to stimulate the formation of plasmin.

Together with a appropriate materials design, a desirable medical device associated with tPA can be capable of destroying or shrinking emboli associated with cardiopulmonary bypass. Recent reports suggest that most of the emboli generated during cardiopulmonary bypass have a significant fibrin component. (19, 20) The body's primary means of degrading fibrin is via tissue plasminogen activator (tPA). tPA is currently in clinical use as a remedy for heart attack and stroke (thrombolysis, reperfusion therapy). This therapy involves delivering tPA through an intravenous line to break up and dissolve a clots in the coronary artery, thereby restoring blood flow. (21) tPA is of particular interest for use with medical devices described herein for providing protection against emboli or the like, based on the high specificity of tPA for clot degradation without causing systemic bleeding events.

Suitable anti-platelet agents include, for example, acetylsalicylic acid, ADP inhibitors, phosphodiesterase III inhibitors, glycoprotein IIB/IIIA inhibitors, adenosine reuptake inhibitors, nitrates, such as nitroglicerin and isosorbide dinitrate, and Vitamin E. Suitable anti-coagulation agents include, for example, heparin, warfarin, and the like. Suitable growth factors include, for example, vascular endothelial growth factor (VEGF) and the like. Generally, suitable forms of these agents are readily available commercially.

In some embodiments, materials are incorporated into the device that form by decomposition a therapeutic composition. For example, nitric oxide (NO) can stimulate beneficial vascular responses. Compounds with an $NONO^-$ functional group can emit nitric oxide following implantation of the medical device. Suitable compositions include, for example, $(CH_3)_2CHNHNONO^-$, $(CH_3CH_2)_2NNONO^-$, $H_2N(CH_2)_3NHNONO^-$, $NaNONONa$. The synthesis of 1-(2S-carboxypyrrolidin-1-yl)-oxo-2-hydroxydiazene disodium salt, 1-hydroxy-2-oxo-3-carboxymethyl-3-methyl-1-triazine N-methylamide disodium salt, 1-hydroxy-2-oxo-3-carboxymethyl-3-methyl-1-triazine N-methylamide sodium salt, the bis(nitric oxide) adduct of L-prolyl-L-leucylglycinamide, and corresponding protein adducts are described in U.S. Pat. No. 5,632,981 to Saavedra et al., entitled "Biopolymer-Bound Nitric Oxide Releasing Compositions, Pharmaceutical Compositions Incorporating Same And Methods Of Treating Biological Disorders Using Same," incorporated herein by reference. Conjugates of heparain, for example with dermatan sulfate, that are effective to prevent thrombosis are described in U.S. Pat. No. 6,491,965 to Berry et al., entitled "Medical Device Comprising Glucosaminoglycan-Antithrombin III/Heparin Cofactor II Conjugates," incorporated herein by reference. Furthermore, some polymers decompose to form an acidic moiety, such as polyhydroxybutyrate degrading to 3-hydroxyvaleric acid. Such acidic agents can retard emboli formation in the vicinity of its release.

In some embodiments pro-coagulation agents may be used. These agents include metals, biological agents or other energetic stimuli. An example of a metal compound is silver nitrate (styptic pencils), which can be used to stem blood flow significant wounds. Other biological materials can produce similar results, for example, collagen or another protein or combination of proteins associated with the coagulation cascade i.e. factor VIIa, Xa, V, XIIIa, Fibrin, Thrombin, von Willepbrand factor (vWF) or other co-clotting factors secreted by platelets or bound from plasma. These agents are meant as examples and are not limiting.

In some embodiments blood clotting may be not advantageous and elution of agents to prevent clot formation may be useful. This can be preformed by associating the medical article with bioactive agents that inhibit or reveres the thrombolytic process, i.e. Heparin Sulfate, Antithrombin II, Protein C, and Tissue Plasminogen Activator.

In other embodiments, the association of anti-microbial agents to help prevent and or treat potential infections associated with medical articles. These agents include without limitation antibiotics, anti-microbial metals. Examples of antibiotics include, for example, penicillin, phosphonomycin, bacitracin and vancomycin, which interfere with cell wall synthesis. In particular, penicillin inhibits a crosslinking reaction in cell wall synthesis. Other antibiotics, such as streptomycin, tetracycline, chloramphenicol and erythromycin, act by inhibiting protein synthesis by binding to bacterial ribosomes. Other suitable antibiotics include, for example, bacteriocins, such as lysostaphin, and peptide antibiotics, such as actinomycin, bacitracin, circulin, fungisporin, gramicidin S, malformin, mycobacilin, polymyxin, tyrocidine and valinomycin.

In other embodiments delivery of bioactive agents to inhibit restenosis of vascular vessels may be desirable. Suitable therapeutic agents to inhibit restenosis include, for example, radioactive atoms/ions, nitric oxide releasing agents, heparin, angiopeptin, calcium channel blockers, angiotensin converting enzyme inhibitors, cyclosporin A, trapidil, terbinafine, colchicine, taxol, c-myc and c-myb antisense, antibodies to SMC mitogen platelet derived growth factor, and the like.

Combinations of two or more bioactive agents of the same class and/or of different classes can be used.

The bioactive agent can be associated with the materials of the embolism protection device by one or more approaches. For example, the device can be contacted with a solution of the agent such that the agent can be infused within the device. The agent is then released, possibly gradually, upon implantation of the device. In other embodiments, the bioactive agents are placed in contact with the polymers during the polymerization and/or a crosslinking/grafting step such that the bioactive agents are incorporated within the polymer matrix. The bioactive agents then elute following implantation. In particular, SCF fibers can take in liquid compositions within the surface capillaries at relatively large volumes for subsequent elution of the composition following delivery of the device. The bioactive agents can be adsorbed into the capillary channels along with a biocompatible adhesive or other control release agent. Elution of the bioactive agent from the adhesive or degradation of the adhesive can release the bioactive agent in a controlled way.

For systemic administration, the therapeutic dose of tPA for a human patient can be 0.01 to 80 micro moles (70-8750 ng/ml) but is thought to be most effective at 500-1000 ng/ml. See, for example, Wu J H and Diamond S L, "Tissue plasminogen activator (tPA) inhibits plasmin degradation of fibrin. A mechanism that slows tPA-mediated fibinolysis but does not require alpha 2-anitplasmin or leakage of intrinsic plasminogen," Journal Clinical Investigation 1995; 95(6):2483-2490. Lower doses may be effective with local delivery since the local concentration can be higher over the delivery period. An appropriate corresponding dose for local delivery can be sustained throughout the time of implant. If the dose is released too quickly, a toxic environment can ensue (>25,000 ng/ml for systemic delivery). See, for example, Hrach C J, Johnson M W, Hassan A S, Lei B. Sieving P A and Elner V M, "Retinal toxicity of commercial intravitreal tissue plasminogen activator solution in cat eyes," Archive Opthalmology 2000 May; 118(5): 659-63. To determine the initial loading dose, the release kinetics of tPA from the device can be used to deliver a desired dose of tPA or other biologically active agent. An empirical evaluation of an appropriate dose can be estimated from in vitro studies, such as the flow loop studies described in copending U.S. patent application Ser. No. 10/414,909 to Ogle, entitled "Embolism Protection Device," incorporated herein by reference, or from animal studies. In some embodiments, it may be desirable to deliver the biologically active agent with a suitable biocompatible carrier. Suitable biocompatible carriers can be, for example, a physiologically buffered saline. Suitable buffers can be based on, for example, the following compounds: phosphate, borate, bicarbonate, carbonate, cacodylate, citrate, and other organic buffers such as tris(hydroxymethyl)aminomethane (TRIS), N-(2-hydroxyethyl) piparazine-N'-(2-ethanesulfonic acid) (HEPES) or morpholine propanesulphonic acid (MOPS). The ionic strength of the biocompatible carrier can be adjusted by the addition of one or more inert salts including, for example, NaCl, KCl and combinations thereof. In some embodiments, the ionic strength is near physiological values.

Additionally or alternatively, genes coding for desired polypeptide-bioactive agents can be delivered in a vector. The vector can be taken up by adjacent cells and expressed as the protein. Suitable vectors are known in the art, and include, for example, viral vectors, plasmids and the like. In particular, a vector encoding tPA can be delivered through the device. The effectiveness of a vector for tPA expression in rabbits is described further in Waugh et al., "Gene therapy to promote thromboresistance: Local over-expression of tissue plasminogen activator to prevent arterial thrombosis in an in vivo rabbit model," Proceeding of the National Academy of Sciences—USA 96(3): 1065-1070 (Feb. 2, 1999), incorporated herein by reference. Vectors, for example, plasmids and viral vectors, suitable for transforming human cells with appropriate control sequences for expression in human cells are described further in U.S. Pat. No. 5,106,741 to Marotti et al., entitled "Tissue Plasminogen Activator (TPA) Analogs," and U.S. Pat. No. 4,935,368 to Ryotaro et al., entitled "Process For Producing Tissue Plasminogen Activator," both of which are incorporated herein by reference.

Delivery and Retraction of the Embolism Protection Device

In general, embolism protection devices can be supplied to medical professionals in a range of sizes, such that an appropriate size can be selected from the available sizes for a particular patient and for a particular point of placement. Due to the expanding nature of the embolism protection device a precise size device is not required since the device conforms over a reasonable range to the vessel. Nevertheless, imaging techniques and estimates from experience and the patient's size can provide an appropriate estimate for the appropriate size of the embolism protection device. An integrated system for the delivery, deployment and extraction of an embolism protection device is described above that is useful for many procedures. Additional approaches are described herein, which may be useful for the same uses and/or of a range of additional uses.

An embolism protection device can be placed within the desired vessel of a patient with a catheter, a syringe, a guidewire or the like. In particular, an embolism protection device can be attached to a guidewire to feed the device through a catheter to a desired position in a vessel within a patient. The guidewire can be separate from the device following the placement of the device, or the guidewire can remain tethered to the device to facilitate maintaining the device at the desired position and/or to facilitate removal of the device. Removal of the guidewire can be performed by pulling out the guidewire if the guidewire is not attached to the device and if the device is applying sufficient force against the walls of the vessel such that friction can hold the device in place. If the guidewire is to remain attached to the device, the guidewire can be attached to the device with a mechanical attachment or with an adhesive. The guidewire can be mechanically attached to the device, for example, by forming the polymer around the end of the wire, generally with a non-straight section of wire, winding the wire around a section of the device and/or heat shrinking a portion of the polymer around the end of the wire.

Figure 31:
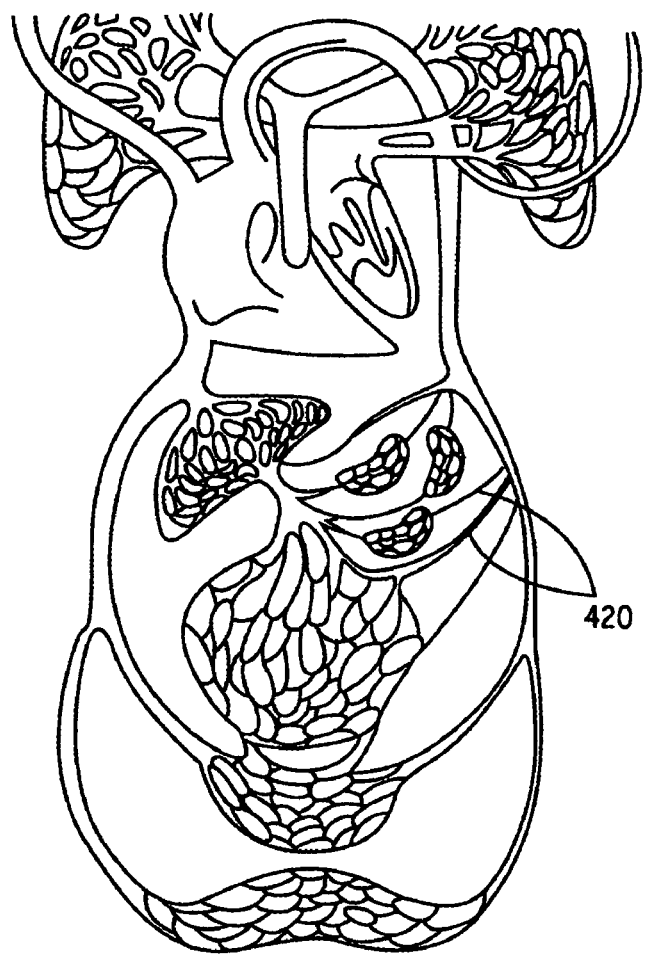
FIG. 31 is a schematic view showing possible positioning of embolism protection devices within a renal vessel.
Figure 30:
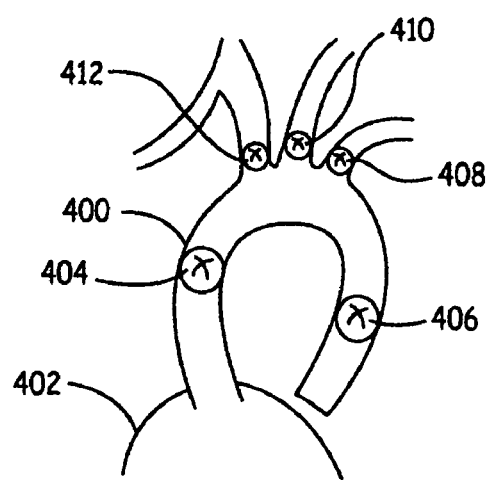
FIG. 30 is a schematic view showing possible positioning of embolism protection devices within an aorta and corresponding branch vessels.

Due to the potentially serious outcomes of cardiac intervention that can result in emboli associated with the aorta, the embolism protection device can be positioned at one or more positions within the aorta or in arteries branching from the aorta. Referring to FIG. 30, aorta 400 is shown adjacent heart 402. As shown in FIG. 30, five embolism protection devices 404, 406, 408, 410, 412 are shown in different positions. Any one or more of these can be used for a particular patient. Devices 404-412 are shown with device 404 in the ascending aorta, device 406 in the descending aorta, device 408 in the innominate artery, device 410 in the left common carotenoid artery and device 412 in the left subclavian artery. Embolism protection devices can be similarly placed within the renal artery 420, the position of which is shown in FIG. 31. One mechanism of deployment of an embolism protection device is shown in FIG. 32, in which embolism protection device 422 is connected to a fixed position along a guide wire 424 such that device 422 can be deployed during a procedure and removed with the same guide wire at the completion of the procedure. Device 422 has a spring 426 such that the device deploys upon release from sheath 428. The device prior to deployment is shown in view A, and the deployed device is shown in view B.

In some embodiments, an embolism protection device can be placed within a coronary artery. In particular, the embolism protection device can be placed down stream from a planned site of intervention, for example, by angioplasty, placement of a bypass graft or introduction of a stent. Referring to FIG. 33, embolism protection device 440 is shown within coronary artery 442 of heart 444. Device 440 is located downstream in the artery from an intervention site 446.

Figure 34:
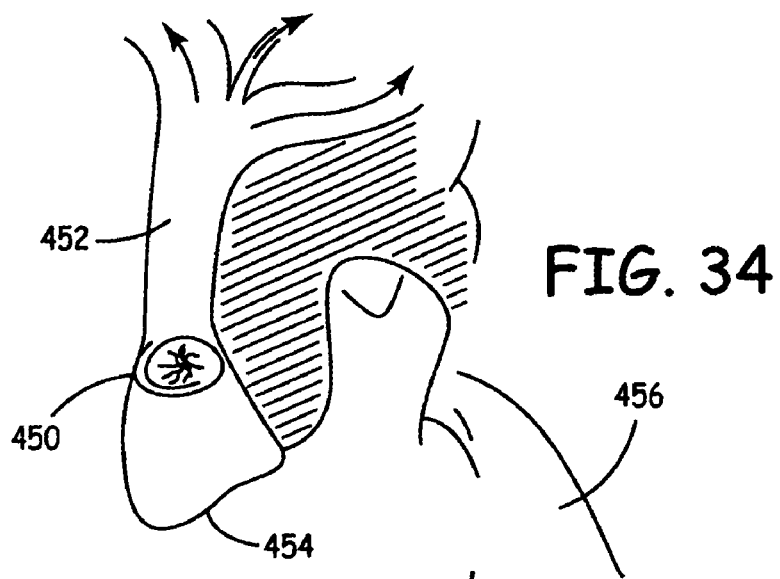
FIG. 34 is a schematic view of an embolism protection device in the pulmonary artery.
Figure 35:
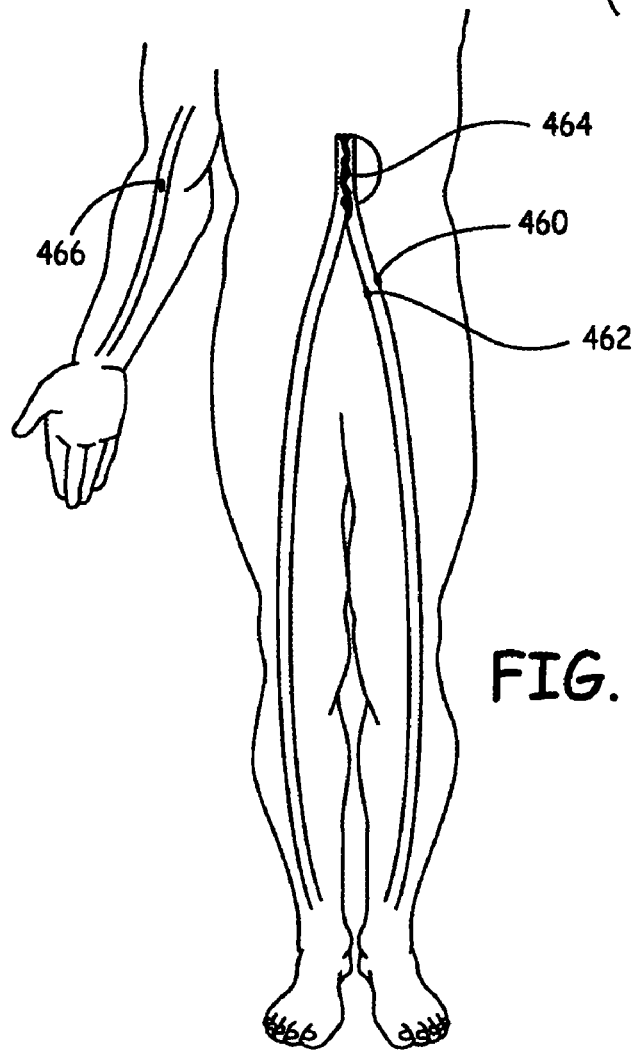
FIG. 35 is a schematic view of an embolism protection devices positioned in blood vessels in a patient's leg and arm.
Figure 36:
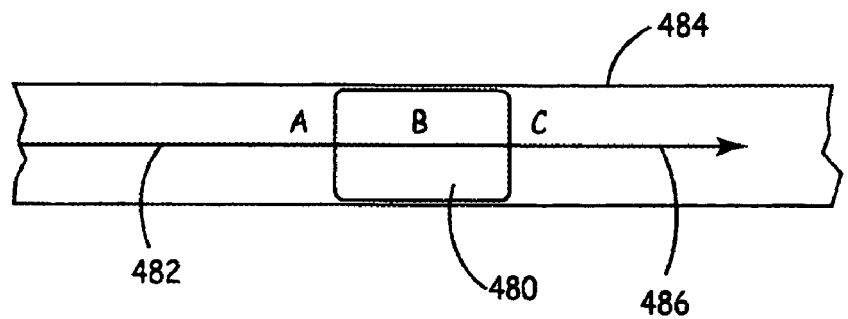
FIG. 36 is a side view of an embolism protection device associated with a guide-wire through which a biologically active agent is delivered at one or more of locations A, B and C.
Figure 37:
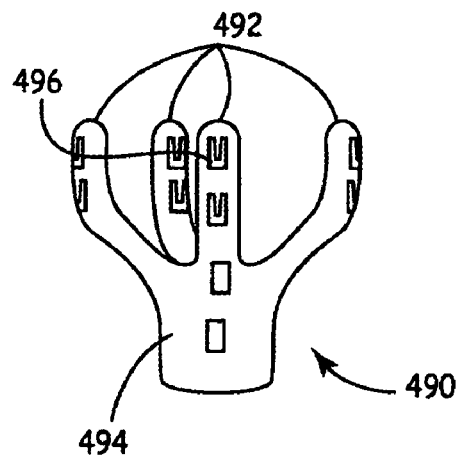
FIG. 37 is a side view of a gripper device to facilitate removal of an embolism protection device.
Figure 38:
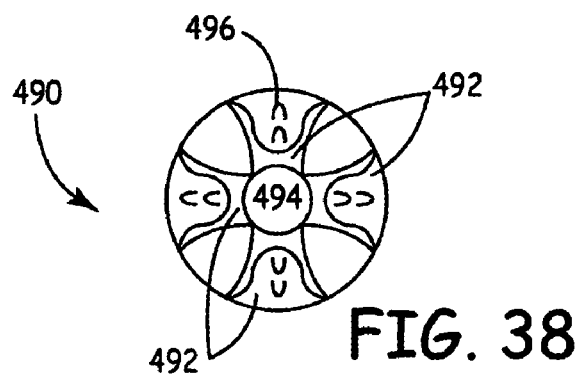
FIG. 38 is a top view of the gripper device of FIG. 37.
Figure 39:
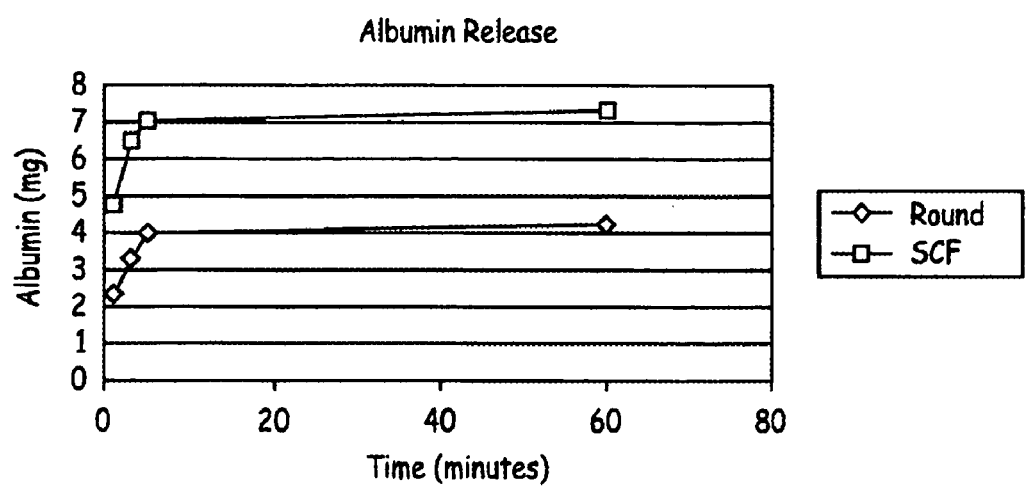
FIG. 39 is a plot of albumin release from a round fiber and an SCF fiber.

In other embodiments, an embolism protection device can be place in the venous side of the heart/vascular system to prevent emboli to the lungs. Referring to FIG. 34, embolism protection device 450 is within the pulmonary artery 452 downstream from the pulmonary heart valve 454 where pulmonary artery 452 attached to heart 456. Flow from the pulmonary artery goes to the lungs. More generally, an embolism protection device can be placed within any vessel in the body. As shown in FIG. 35, devices 460, 462 are within arteries leading to the leg from the descending abdominal aorta 464 while device 466 is in an arm. Embolism protection devices can be similarly placed in veins.

As noted above with respect to FIG. 13, the embolism protection device can comprise two distinct portions or similarly can be used with a separate but associated drug delivery article. The elution of a bioactive agent from the embolism protection device is described above. Additionally or alternatively, one or more bioactive agents can be delivered through a guidewire or the like tethered to the embolism protection device. The guidewire can have a small inner channel that has an opening into the vessel at or near the proximal end. The flow rate and time determines the dose of biologically active agent delivered into the vessel. Referring to FIG. 36, embolism protection device 480 associated with guidewire 482 is within a body vessel 484. Guidewire 482 has a small internal channel that can have an opening at point A, B and/or C. The natural flow direction in the vessel is indicated by arrow 486. Delivery of a biologically active agent at point A results in the flow of the agent through device 480 and downstream. Delivery of the agent at point B results in a concentration of the agent within the device with any residual agent flowing downstream. In addition, delivery of the agent at point C results in delivery of the agent downstream from the device.

Once the embolism protection device has served its purpose, it may be desirable to remove the device or a portion thereof. For example, shortly after completing a procedure, the device may have had the opportunity to collect and/or dissolve the emboli of significance. Alternatively, once the embolism protection device has completed eluting a biologically active agent following the trapping and/or dissolving of emboli associated with a procedure or other event, it may be desirable to remove the device. Removal of the device can take place, for example, minutes, hours, days, months or years following delivery depending on the particular device and its intended purpose.

As noted above, in some embodiments, an embolism protection device can be attached to one or more tethers or the like such that pulling on the tethers tends to reduce the size of the device such that it can be moved upstream from its delivered position. In other embodiments, an embolism protection device can have a reduced diameter or pointed tip at the proximal end. With a reduced diameter proximal end and a compressible polymer structure generally possessed by the device, the device can be pulled within a sheath using a tether due to the forces applied to the device at the end of the sheath. Once the device is confined within the sheath, the device can be withdrawn from the vessel with the sheath.

In alternative or additional embodiments, an extraction device can be used to facilitate removal of the embolism protection device. An extraction device comprises a gripper that can grip the embolism protection device and reduce the diameter of at least a portion thereof. In some embodiments, the gripper can have barbs that facilitate the removal of the embolism protection device. The gripper can be positioned within the vessel through a catheter or the like. An actuating wire or other control device can connect the gripper with a control handle at the proximal end of the gripper device outside of the patient. Thus, the gripper can be manipulated by a health care professional from outside of the patient using appropriate visualization techniques, such as a fiber optic based visualization systems for minimally invasive surgical procedures.

An embodiment of a suitable gripper is shown in FIGS. 37 and 38. Gripper 490 has a gripping portion with four flexible arms 492 extending from a shaft 494. Shaft 494 can have a hollow core for threading the shaft over a guide-wire or the like. Arm 492 can include barbs 496. An outer shaft can move in position relative to shaft 494. Outer shaft can engage arms 492 and deflect them toward the center of shaft 494. This deflection of arms 492 results in a gripping function. Thus, if arms 492 are positioned along the outer surface of an embolism protection device, the deflection of arms 492 toward a center axis compresses the embolism protection device correspondingly. This deflection can be continued until the gripper and the embolism protection device has a small enough profile for removal from the vessel. For embodiments of an embolism protection device with a plurality of sections, gripper 490 can be used to facilitate removal of a portion of the embolism protection device oriented toward the gripper. Furthermore, various other gripper configurations, including, for example, some configurations developed for use with catheters for other functions can be adapted for use in removing an embolism protection device.

EXAMPLES

Example 1

SCF Fibers Biological Agent Absorption and Delivery a. Loading the Fiber

This example demonstrates the capacity of SCF fibers to deliver higher quantities of biologically agent than round fibers. In this experiment, bovine serum albumin (albumin) was used. Albumin, a biological serum protein, was chosen because it has a similar molecular weight to that of TPA.

Two different cross-sectional geometries were evaluated. Group #1 consisted of standard round fibers and group #2 insisted of the SCF fibers (specifically 4DG™ fibers, Fiber Innovation Technology, Inc. Johnson City Tenn.). The cross sections of the fibers are shown schematically in FIGS. 1 and 2. Both fiber were six denier polyester fibers with similar surface finishes. Six-fiber bundles (3 from each group) of approximately the same size were weighted. (See Table 1.) Samples were labeled and placed in 15 ml polymer BD Falcon® centrifuge tube. A 5 ml quantity of (4 mg per ml albumin solution prepared from Bovine Serum Albumin solid form 99% Sigma Chemical Co.) was added to each tube. Fiber bundles were incubated in the albumin solution for ~3 minutes. During this time, the tubes were shaken at 50 rpm. The fiber bundles were then removed from the tubes and reweighed to determine the absorption of albumin solution. (See Table 1.)

TABLE 1

Weight of fiber Bundles

| | Sample # | Pre (mg) (Fiber bundle) | Post (mg) (Fiber bundle + absorbed albumin sol.) | X times increase | Change (mg) (albumin sol.) | *Converted wt to ml of | Volume (ml)/mg of fabric |
|---|---|---|---|---|---|---|---|
| Round 6 denier | 1 | 235.9 | 2735.3 | 11.6 | 2499.4 | 2.4033 | 10.2 |
| | 2 | 182.2 | 1919.4 | 10.5 | 1737.2 | 1.6704 | 9.2 |
| | 3 | 161.8 | 2466.0 | 15.2 | 2304.2 | 2.2156 | 13.7 |
| | average | 193.3 | 2373.6 | 12.3 | 2180.3 | 2.0964 | 10.8 |
| SCF 6 denier | 4 | 149.1 | 3041.5 | 20.4 | 2892.4 | 2.7812 | 18.7 |
| | 5 | 247.6 | 4309.2 | 17.4 | 4061.6 | 3.9054 | 15.8 |
| | 6 | 187.7 | 3580.3 | 19.1 | 3392.6 | 3.2621 | 17.4 |
| | average | 194.8 | 3643.7 | 18.7 | 3448.9 | 3.3162 | 17.0 |

Figure 40:
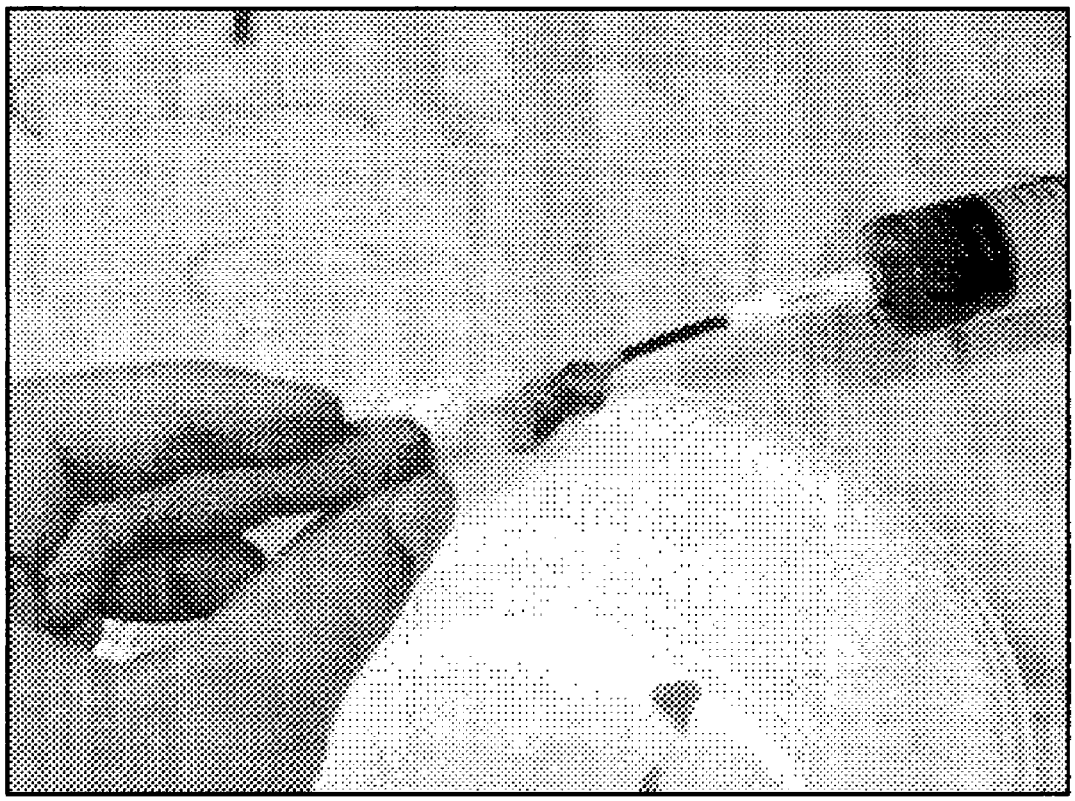
FIG. 40 is a photograph of a SCF fiber associated with a dye.

*The solution was 4 mg of albumin per 1 ml of aqueous PBS thus the density was calculated as 1.04 g = 1 ml of solution The data from Table 1 demonstrates an increased absorbency of solution; 17.0 ml albumin solution/mg of fabric (SCF) vs. 10.8 ml albumin solution/mg of fabric (round) an increase of 62%. Thus the average dose delivered in each group is a follows; round 2.1 ml of a 4 mg/ml solution of albumin which equals 8.4 mg albumin, SCF 3.3 ml of a 4 mg/ml solution of albumin which equals 13.3 mg albumin. This data suggests that the SCF fiber can absorb a greater quantity of aqueous solution thus can carry and deliver a greater quantity of biological agent.

b. Delivery Experiment:

The fiber bundles, which had been incubated in the albumin solution (see above) were then placed into new 15 ml centrifuge tubes, which contained 10 ml of Phosphate Buffered Saline (PBS) pH 7.4 (Sigma Chemical Co.). The samples were then shaken at 50 rpm for various time points (1, 3, 5 and 60 minutes). Then, at each time point, the fiber bundles were transferred to new 15 centrifuge tubes containing PBS (10 mls).

Solutions were assayed for their concentration of albumin using Bicinchonic Acid (BCA) Method to determine protein concentrations. This assay relies on the protein's amino acids (cysteine, cystine, tryptophane and tyrosine) to react with copper (Cu+2) which is converted to its cuprous form (Cu+1). The BCA is very highly sensitive and selective for Cu+1 cations, and the reaction forms as a soluble purple conjugate, which is measurable by spectroscopic methods at 562 nm. Known standards of Albumin solution were used to make up the calibration curve ranging from 2,000 μg/ml-0 μg/ml). 25 microliters (μl) of solution and standard was added to a 96 well plate a along with 200 μl of working solution from Pierce Chemical Co. containing pre-measured quantities of BCA and Copper (Cu2+). Samples were prepared in duplicate. Samples were placed in an incubator at 37° C. for 30 minutes. The plate was read with a Power Wave X-1 spectrophotometer, and intensities for each well were reported. The calibration curve was used to calculate the concentration from the intensities generated by the spectrophotometer. The concentrations were averaged in Table 2 (Ave.=average and SD=standard deviation).

TABLE 2

| BCA Assay Results | | | | | | | |
|---|---|---|---|---|---|---|---|
| | | Calibration Cure R2 = 0.999 | | | | | |
| Time Points | Sample | 1 min | 3 min | 5 min | 60 min | Total Albumin | % delivered |
| Round 6 denier | 1 | 168.5 | 100.5 | 87.2 | 41.5 | 4.0 | 39.8 |
| | 2 | 234.5 | 50.5 | 47.5 | 60.5 | 3.9 | 56.6 |
| | 3 | 283.2 | 149.9 | 34.9 | 13.2 | 4.8 | 52.2 |
| | Ave. | 228.8 | 100.3 | 56.5 | 38.4 | 4.2 | 49.5 |
| | SD | 57.6 | 49.7 | 27.3 | 23.8 | 0.5 | 8.7 |
| SCF 6 denier | 4 | 431.2 | 171.2 | 76.2 | 24.2 | 7.0 | 60.8 |
| | 5 | 552.2 | 182.5 | 44.9 | 37.5 | 8.2 | 50.3 |
| | 6 | 445.2 | 159.2 | 43.9 | 9.5 | 6.6 | 48.5 |
| | Ave. | 476.2 | 171.0 | 55.0 | 23.8 | 7.3 | 53.2 |
| | SD | 66.2 | 11.7 | 18.4 | 14.0 | 0.8 | 6.7 |

The data demonstrates that the SCF fiber can deliver a greater quantity of Albumin. (See FIG. 39.) While the slope of the curve and percent delivered by the SCF fibers is larger than the round fibers there were no statistically meaningful differences.

Example 2

Solution Tracking Along the Fibers Grooves

The following example demonstrates the feasibility of applying a biological agent, which will track along the grooves in the fiber to provide greater agent availability within the device. This experiment will demonstrate that a round fiber did not provide similar increased agent availability. Two different cross-sectional fiber geometries were evaluated. Group #1 fibers were standard round fibers, and group #2 fibers was the SCF fibers (specifically 4DG™ fibers, Fiber Innovation Technology, Inc. Johnson City Tenn.). Both fiber types were six denier polyester fibers with similar surface finishes. Two bundles of fibers were aligned. The fibers were bound at both ends and then compressed slightly to formulate a bulb like appearance. One end of the fibers was then attached to a syringe, which contained Coomassie Blue (CB) (Coomassie Brilliant Blue Bio-Rad Labratories, Hercules, Calif. 94547 in distilled water). The dye was injected into the fibers. At which time photographs were taken and observations were recorded as to the content and coverage the die had in each set of bundles. (See FIG. 40.)

Results

Figure 41:
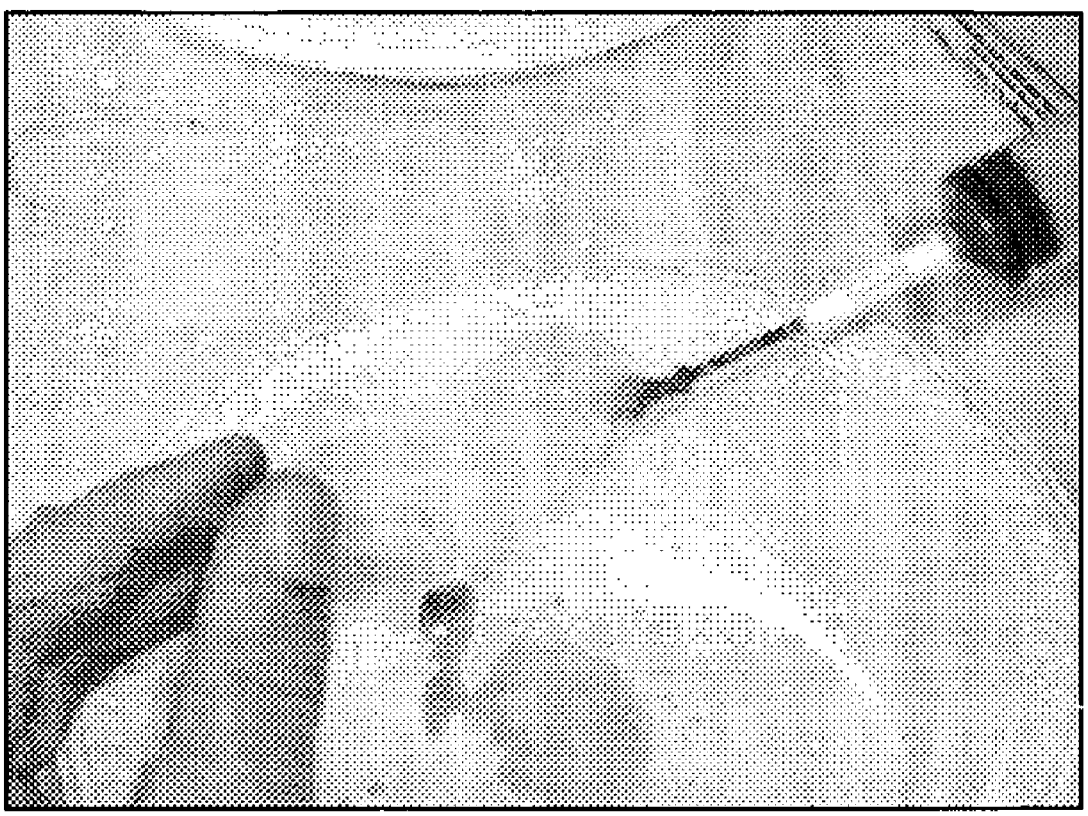
FIG. 41 is a photograph of a round fiber associated with a dye.

The CB dye tracked along the SCF fibers very quickly and had a visibly higher quantity of coverage than the round fibers. This diffuse coverage of the fiber bundles demonstrates the surface capillary action of the SCF fibers. The dye indiscriminately dripped down the round fibers with little tracking. (See FIG. 41.) It can be concluded that the lack of intimate contact between the round fiber and the agent containing solution will result in random diffusion and the biological agent can be washed away.

Example 3

Evaluation with an In Vitro Flow Loop

This example demonstrates the utility of an in vitro flow loop for evaluation of an embolism protection device as well as provides an evaluation of two embodiments of an embolism protection device, one with incorporated tPA and one without incorporated tPA.

The interrupted flow loop was developed to mimic the environment of a native coronary artery. The apparatus consisted of four components: a circulation unit, the embolism protection device, the blood/media, and the emboli. The flow loop was constructed as indicated in FIG. 42. The circulation unit had a heated reservoir 500 holding blood and media 502, tubing 504, a pump 506, injection ports 508, 510 and a collection vessel 512. Embolism protection device 514 was held in a fixture 516 within tubing 504. Flow through the system is noted in FIG. 42 with four flow arrows.

Embolism protection device 514 was formed with two sections of structure. The layered system for purposes of this experiment was a polymeric construct that could both release tPA and trap the emboli based on an appropriate porosity. Referring to a schematic view of a pre-hydrated device 514 in FIG. 43, a first layer 520 was a nylon mesh polymer with a 70 micron pore diameter obtained from Sefar America Inc. Depew, N.Y. Layer 520 served to entrap emboli. A second layer 522 was a sponge-like layer made of polyacrylamide and impregnated with tPA. To incorporated tPA into layer 522, a solution was prepared comprising of 1.5 ml-5 weight % acrylamide solution (approximately 2.67% acrylamide final concentration based on a volume per volume dilution), 6 μl-human single-chain tPA (2.2 mg/ml, Molecular Sciences, MI), 9 μl-10% ammonium persulfate and 6.7 μl-TEMED. Three aliquots of 0.5 ml gels were made in glass test tubes and allowed to polymerize for 1 hr at room temperature, thus creating three gels. Following polymerization, each gel had a total tPA content of 500 ng at a concentration of 1,000 ng/ml). The gels were removed from the tubes, and the nylon mesh layer was wrapped around the flat end and the sides of each gel leaving the rounded end of the gel from the bottom of the tube uncovered. Each device when placed within the flow loop was positioned with the flat end down-stream and with the round end upstream such that emboli are trapped by the mesh within the gel. Following contact with an aqueous solution, the gel expanded to approximately twice its volume, as is schematically shown in FIG. 44, while the nylon mesh remains essentially unchanged, although it expands in response to the expansion of the gel. Due to the expansion of the gel, the pore size of the mesh may enlarge, but this enlargement was not directly measured.

Figure 45:
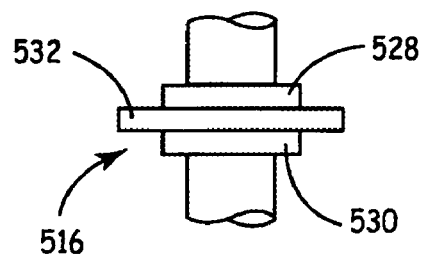
FIG. 45 is a side view of an embodiment of a mount for supporting an embolism protection device within a flow loop.

Three two-layer embolism protection devices were constructed with tPA incorporation, and three two-layer devices were constructed without tPA incorporation using the solution described above except with no tPA. For these tests, a selected device 514 was held by the test fixture 516. Referring to FIG. 45, test fixture 516 had two rings 528, 530 held together with a joining ring 532. Edges of device 514 are gripped between rings 528, 530 to fix device 514 in place.

Circulation of the media was performed with a centrifugal pump capable of generating flows from 30-120 ml/min. The tubing was a vinyl polymer with an inner diameter from 4-6 mm, similar to that of the native arterial vessels. The experiment was accomplished in a test chamber at 37° C. Injection port 508 upstream from the embolism protection device was used to introduce the test emboli. The medium flowing through the system was phosphate buffered saline (PBS). Emboli were generated by placing 1 ml of pig animal blood in a 5 cc syringe and allowing it to clot. Coagulated blood was extruded from the syringe and cut to uniform size (200-225 μm diameter); these uniform coagulated blood fragments will be referred to as "emboli." The flow loop was validated using a calibrated flow meter.

The emboli were introduced into the flow system at a concentration of approximately 15 emboli/ml of buffered saline. The time line for the testing was as follows:

0 time—introduction of device
1 sec.—Begin flow of media (buffered saline)
10 sec—Measure flow rate
15 sec—Inject emboli
30 sec—Collect aliquot #1 (of effluent, i.e. media past device.)
60 sec—Collect aliquot #2
100 sec—Collect aliquot #3
200 sec—Collect aliquot #4
300 sec—Collect aliquot #5

After about five minutes, the flow was stopped and the device removed and photographed microscopically. The device was then fixed for histological analysis. Aliquots of collected liquid were analyzed for emboli. The fixed device was snap frozen, sectioned and placed on a slide for histological analysis. Sections were stained immunohistochemically for fibrin.

As described above, six prototypes for each design (3 with tPA and 3 without tPA) were loaded in the flow loop. Emboli entrapment and dissolution was evaluated in three different ways. First, flow measurements were made at different flow rates to determine the degree to which the device retarded flow. Results are outlined in the following table.

TABLE 3

|  | No Device | Media Mesh Only | Prototype Device |
|---|---|---|---|
| 30 ml/min | 30.3 ± 0.6 | 30.0 ± 1.0 | 28.7 ± 0.6 |
| 60 ml/min | 60 ± 0.0 | 59.3 ± 0.6 | 58.3 ± 1.5 |
| 120 ml/min | 119.7 ± 0.6 | 117.3 ± 2.5 | 114.3 ± 2.1 |
| (120 ml/min) | #1 | #2 | #3 |
| Samples w/out tPA | 118 | 116 | 115 |
| tPA | 117 | 115 | 112 |

Second, the PBS was collected. The total collected effluent was passed over a 0.22 μm filter, and the filter was analyzed via light microscopy for presence of emboli. The effluent had no observable emboli after passing through any of the six devices. This demonstrated that the devices were effective to trap the emboli without blocking the flow.

Third, two portions of the embolism protection device were prepared for histological archiving—one frozen and one paraffin embedded. Selected samples were sectioned and prepared for immunohistochemistry as follows. Sections were postfixed for 2 minutes in 100 mmol/L tris-buffered 1% paraformaldehyde containing 1 mmol/L EDTA, pH 7.2, and rinsed with three changes of phosphate buffered saline, pH 7.2. Porcine fibrin decomposition via tPA thrombolysis was detected using murine antibodies specific for neotype beta-chain fibrin (Mouse Anti-Human, Cross-reacts with pig, American Diagnostica, Inc., Greenwich, Conn., Cat 350, 1:100 dilution, rhodamine conjugated, monoclonal IgG-1) and CD41 platelet glycoprotein IIa/IIIb (Mouse Anti-Human, Cross-reacts with pig, DakoCytomation, Carpinteria, Calif., Cat M7057, 1:100 dilution, FITC conjugated, monoclonal IgG-1). The antibodies listed above were diluted in phosphate buffered saline containing 5% bovine serum albumin (Sigma Chemical Co.) and applied to sections for 30 minutes. Then, the section was rinsed with phosphate buffered saline. All sections were cover-slipped with a 1:8 dilution of Vectashield-DAPI (4,6-diamidino-2-phenylindole) in phosphate buffered saline (Vector Laboratories) and evaluated using an epifluorescence microscope.

Figure 46A:
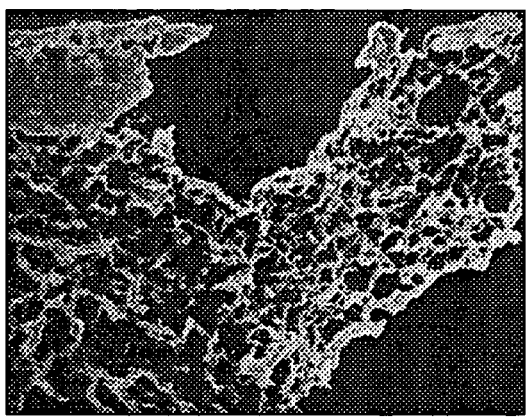
FIG. 46A is a micrograph of a fibrin emboli recovered from an embolism protection device that released tPA, at a magnification of 200×.
Figure 46B:
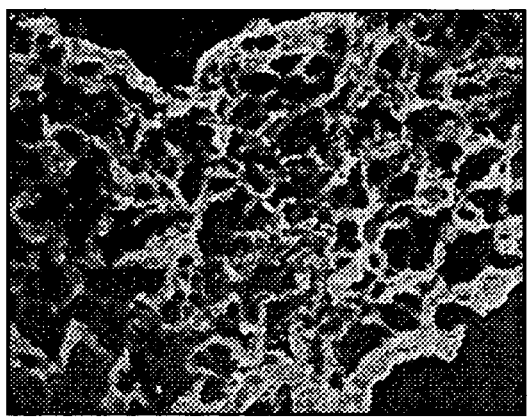
FIG. 46B is a micrograph of the fibrin emboli in FIG. 46A at a magnification of 400×.
Figure 46C:
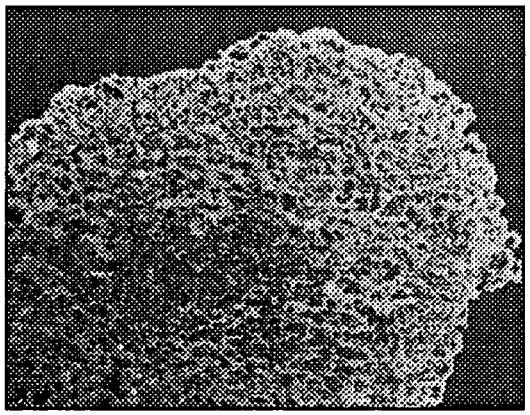
FIG. 46C is a micrograph of a fibrin emboli recovered from an embolism protection device that did not released tPA, at a magnification of 200×.
Figure 46D:
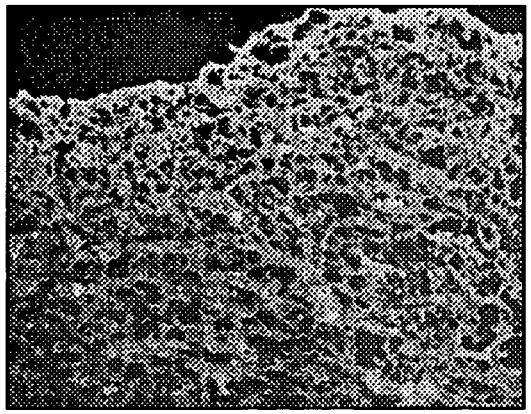
FIG. 46D is a micrograph of the fibrin emboli in FIG. 46C at a magnification of 400×.

Stained fibrin was analyzed and scored on a scale of 1-5; 1 being fully intact and 5 being fully dissociated. FIGS. 46A and 46B are fibrin recovered from the embolism protection device releasing tPA, while FIGS. 46C and 46D show fibrin at the same magnification recovered from an embolism protection device not releasing tPA. As seen in FIGS. 46A and 46B, fibrin treated with tPA was dissolved away to remove significant portions of the structure and to leave relatively large pores in comparison with the equivalent fibrin in FIGS. 46C and 46D that was not treated with tPA.

Results clearly showed degradation of the emboli associated with the device in the treated group and intact emboli in the devices which were not prepared with the tPA. These results show that the tPA eluting from the devices was effective to shrink the emboli.

Example 4

In Vitro Flow Loop with Synthetic Emboli to Determine Entrapment Efficiency

This example demonstrates the effectiveness of the EPD device fabricated from 4DG fibers to entrap synthetic emboli of various sizes in an in vitro flow loop. In these experiments synthetic emboli were used to determine the entrapment efficiency.

Figure 47A:
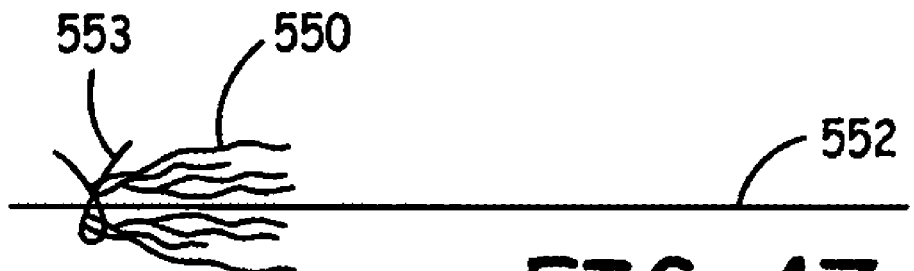
FIG. 47 is a schematic view of the formation and deployment of a device using SCF fibers associated with a guide wire with views A-C depicting steps in the formation and view D depicting the deployment.
Figure 47B:
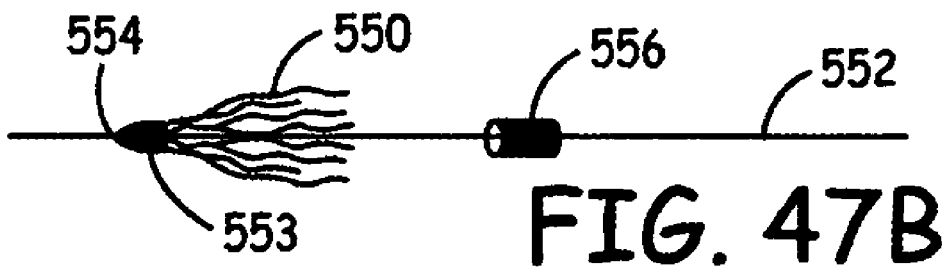
Figure 47C:
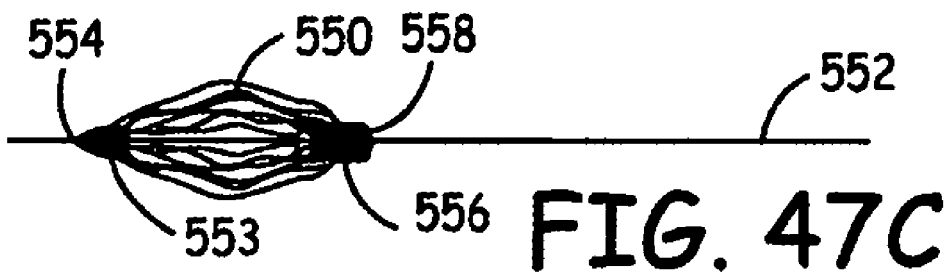
Figure 47D:
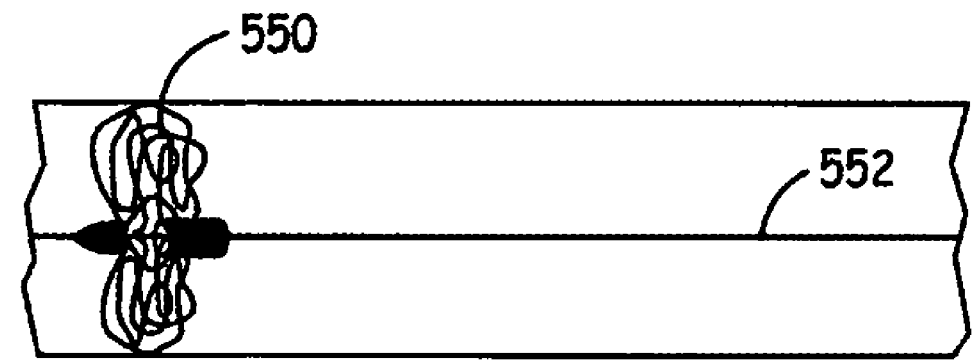

Three devices were configured from, ~100 mg of 6, 14, and 20 denier, 4DG fibers (Fiber Innovation Technology, Inc. Johnson City, Tenn.) approximately 20 mm long, the fiber were all aligned in a similar direction. Fibers 550 were secured 1 inch from the end of a 12 inches long 0.014 stainless steel guide wire 552 (Eagle Stainless Tubing & Fab Inc, Frankin Mass. 02038), as shown in FIG. 47A. The attachment was performed with a polymeric ligature 553, then the distal end was glued with cyanoacrylate (CA) 554 (FIG. 47B). A polymeric sliding collar 556 was placed on the wire 552, the proximal ends of fibers 550 were attached to collar 556 with CA glue 558. (See FIG. 47C.) A sheath catheter was placed over the device. The device was placed into the introduction port. The device was freed from the sheath catheter and the guide wire was pulled to deploy the device within the vessel lumen, as shown in FIG. 47D. Emboli with the following specifications were purchased from Biosphere Medical Rockland Mass. 02370: the emboli size was 40-120 mm, 0.1 ml contained ~16,250 emboli, the polymeric composition was a protien—PVA copolymer. The emboli were incubated in a solution containing Comassie Blue (CB) (Comassie Brilliant Blue Bio-Rad Laboratories, Hercules, Calif. 94547 in distilled water). The CB stains the emboli to make then more visible to facilitate detection.

The device was deployed into the flow loop (which was previously described). The flow rate was 100 ml per minute. The circulating solution was glycerol 33% made from pure glycerol to simulate the viscosity of blood. The device was perfused for 1 minute after which time 0.1 ml of the emboli solution was introduced. The flow was continued for 1 minute after emboli release. Flow was measured at various points during the experiment. An in-line filter (cellulose acetate 0.2 mm) was used to filter the effluent in an effort to detect distal emboli. Following the experiment the device was removed and evaluated with standard light microscopy techniques.

Results

Figure 48:
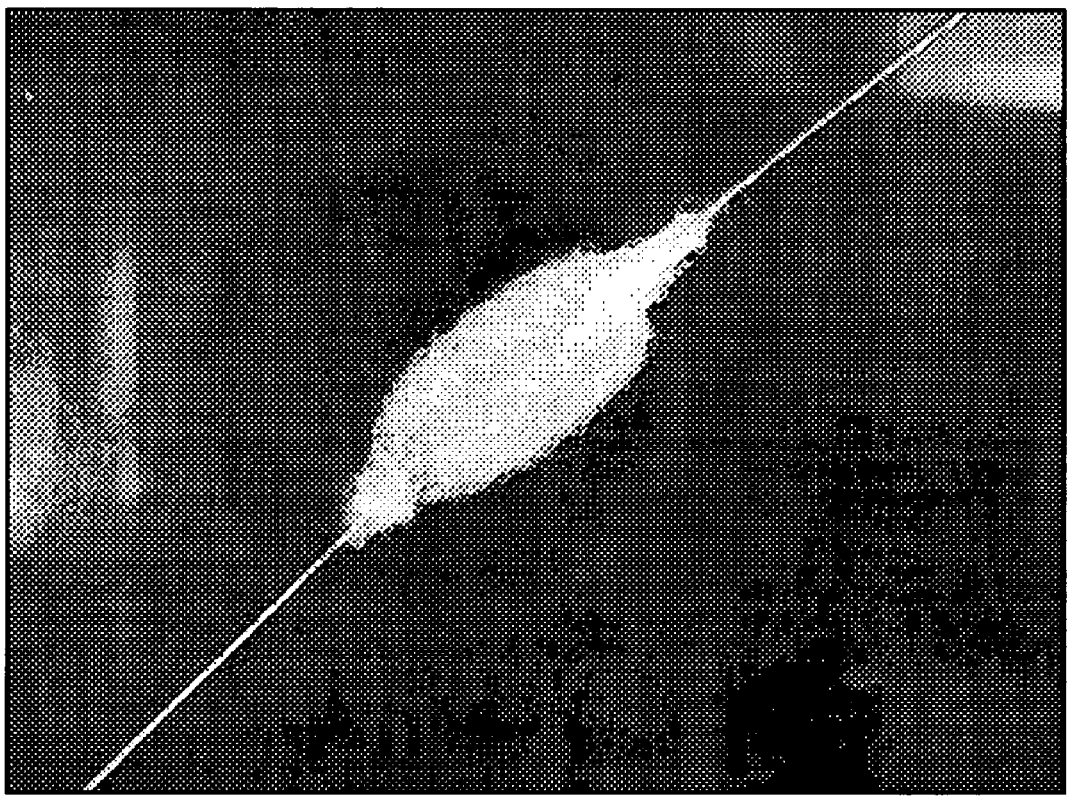
FIG. 48 is a photograph of an embolism protection device with fiber matrix.
Figure 49:
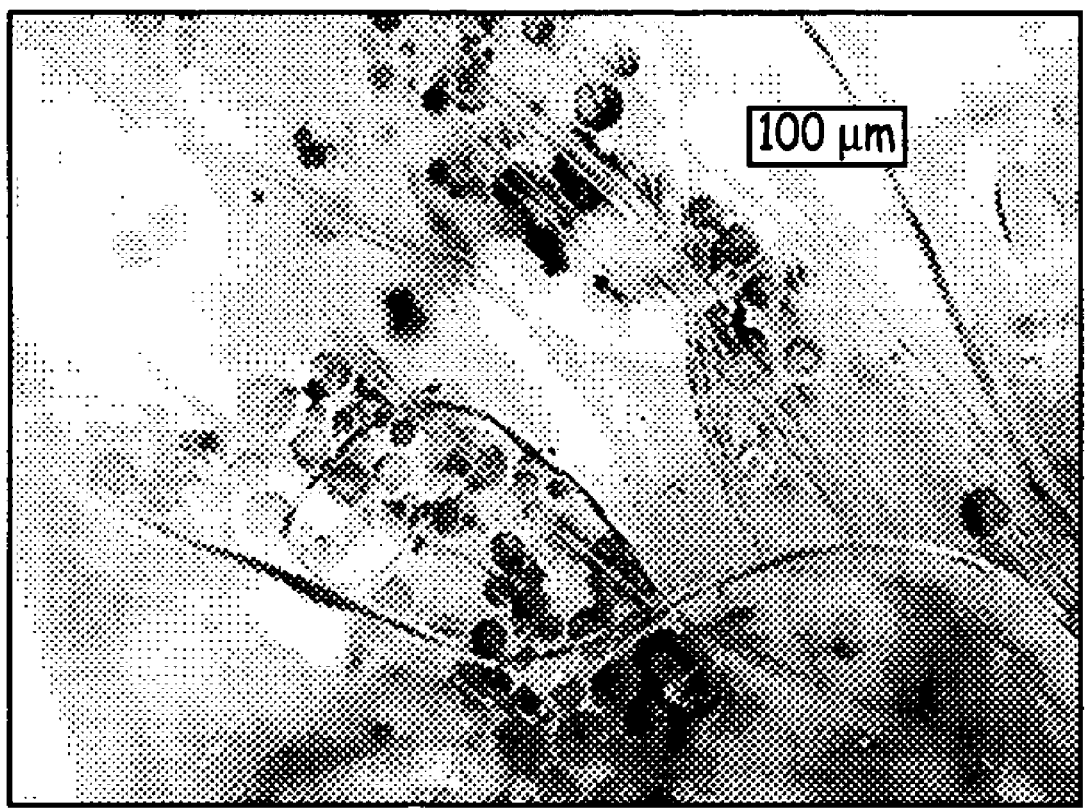
FIG. 49 is a micrograph of the embolism protection device of FIG. 48 with entrapped emboli.

The flow did not change at any point during the experiment, pre to post deployment of the devices or post emboli introduction. The 6 denier device entrapped all the emboli, see table. Visually the majority of the emboli were in the first ⅓ to >½ of the EPD. A photograph of the device is shown in FIG. 48. The distribution was further determined by photomicrographs. A micrograph clearly showing entrapped emboli is presented in FIG. 49. The 14 and 20 denier entraped significant numbers but not complete entrapment like exhibited by the 6 denner fibers. This was a very aggressive test because there evidently are no published reports of emboli less than 100-micron ever being entrapped. Thus, the ability of the EPD to entrap such small emboli significantly improves the device function. This was significantly better than other devices tested under similar test conditions in the published literature (Muller-Hulsbeck S et al. J Vasc Intervent Radiol. 2003 May; 14 (5); 613-20). The fibers can be associated with a biologically active agent prior to delivery to provide treatment along with the physical entrapment of the emboli, as described above.

Example 5

Blood Flow Experiment

In this experiment the flow loop was used to evaluate the fiber matrix device under flow conditions with porcine blood.

A device was fabricated using the same methods in Example 4. The flow loop previously described in FIG. 42 was use to test the in vitro hemodynamics of the device. The flow rate was 100 ml per minute. The circulating solution was 1 liter of fresh hepranized porcine blood. The solution was allowed to circulate for 15 minutes. The flow was measured at various time points.

Results

The flow rate was not measurably changed over the 15-minute perfusion interval. No visible clots were seen on the device over time, or at the end of the exposure.

Example 6

Retraction of the Device

This experiment demonstrates the functionality of using the retraction element to remove the EPD.

A device was fabricated using the same methods in Example 4. The flow loop previously described in FIG. 42 was use to simulate the vasculature. The flow rate was 100 ml per minute. The circulating solution was 1 liter 33% glycerin. The device was introduced and deployed. The solution was allowed to circulate for 1 minute. Porcine thrombolitic emboli were generated by the methods seen above Example 3. The flow was measured at various time points. An in line filter (cellulose acetate 0.2 mm) was used to filter the effluent was used to detect distal emboli.

A retraction device was fabricated out of Nitonal tubing, by laser cutting (LSA Laser Minnetonka Minn.). The arms of the device were heat set with a jig to form an hour glass shape. This device was introduced into the flow loop and used to retrieve the EPD.

Results

The device was successfully compressed, retrieved and brought back throught the introduction port. Also, there was no evidence that emboli were dislodged during this procedure. The flow rate was not measurably changed over the 15 minute time frame.

The embodiments described above are intended to be exemplary and not limiting. Additional embodiments are within the claims. Although the present invention has been described with reference to preferred embodiments, workers skilled in the art will recognize that changes may be made in form and detail without departing from the spirit and scope of the invention.

LITERATURE CITED

All of which are Incorporated by Reference in their Entirety as Well as for the Specific Disclosure Noted 1. Barbut D, Yao F, Lo W, Dilverman R, Hager D N, Trifiletti R R, Gold J P. Determination of size of aortic emboli and embolic loading coronary artery bypass grafting. Ann. Throac. Surg. 1997; 63:1262-7.
2. Barbut D, Caplan L R. Brain complications of cardiac surgery. Curr. Probl. Cardiol. 1997 September; 22(9):449-80.
3. Wolman R L, Nussmeier N A, Aggarwal A, Kanchuger M S, Roach G W, Newman M F, Mangano C M, Marschall K E, Ley C, Boisvert D M, Ozanne G M, Herskowitz A, Graham S H, Mangano D T. Cerebral injury after cardiac surgery: identification of a group at extraordinary risk. Multicenter Study of Perioperative Ischemia Research Group (McSPI) and the Ischemia Research Education Foundation (IREF) Investigators. Stroke 1999. March; 30(3):514-22.
4. Schoen F J. Interventional and Surgical Cardiovascular Pathology. Page 13. W.B. Saunders Company, Philadelphia, Pa. 1989.
5. Llinas R, Barbut D, Caplan L R. Neurologic complications of cardiac surgery. Prog. Cardiovasc. Dis. 2000 September-October; 43(2):101-12.
6. Barbut D, Lo Y W, Gold J P, Trifiletti R R, Yao F S, Hager D N, Hinton R B, Isom O W. Impact of ebolization during coronary artery bypass grafting on outcome and length of stay. Ann. Thorac. Surg. 1997 April; 63(4):998-1002.
7. Bick R L. Hereditary and acquired thrombophilia: preface. Semin. Thromb. Hemost. 1999; 25:251-253.
8. Fasseas P, Orford J L, Denktas A E, Berger P B. Distal protection devices during percutaneous coronary and carotid interventions. Curr. Control Trials Cardiovasc. Med. 2001; 2(6):286-291.
9. Mohammad S F. Enhanced risk of infection with device-associated thrombi. American Society of Artificial Internal Organs J. 200 November-December; 46(6); S63-8.
10. Allcock H R, Lampe F W. Contemporary Polymer Chemistry. Page 8 Second edition Prentice Hall, Engle Cliffs, N.J., USA 1990.
11. Chapiro, A. Radiation Chemistry of Polymer Systems. Interscience, New York, 1962.
12. Bos G W, Poot A A, Beugeling T, Van Aken W G, Feijen J. Small-diameter vascular graft prostheses: current status. Arch. physiol. Biochem. 1998 April; 106(2): 100-15.
13. Chu C, Vonfaunldofer J A, Greisler H P. Wound Closure Biomaterials and Devices. CRC Press New York 1996.
14. Karadag E, Saraydin D, Caldiran Y, Guven O. Swelling studies of copolymeric Acrylamide/crotonic acid hydrogels as cariers for agricultural uses. Polymers for Advanced Technologies 2000 February; 11(2):59-68.
15. Kim S W, Bae Y H, Okano T. Hydrogels: swelling, drug loading, and release. Pharm. Res. 1992 March; 9(3):283-90.
16. Gehrke S H, Andrews G P, Cussler E L. Chemical aspects of gel extraction. Chemical Engineering Science 1986; 41:2153-2160.
17. Trimnell D, Fanta C F. Formulations Prepared from Polyacrylamide and Starch. J. Polym. Mater. 1994; 11:271-277.
18. FDA Document number 02D-074 Denture Cleaners, Adhesives, Cushions, and repair materials:5. Polyacrlamide polymer denture adhesive (21 C.F.R. 872.3480).
19. Reichenspurner H, Navia J A, Berry G, Robbins R C, Barbut D, Gold J P, Reichart B. Particulate emboli capture by an intra-aortic filter device during cardiac surgery. J. Thorac. Cardiovasc. Surg. 2000 February; 119(2):233-41.
20. Harringer W, Capture of particulate emboli during cardiac procedures in which aortic cross-clamp is used. Ann. Thorac. Surg. 2000 February; 119(2)701119-23.
21. Verstraete M. The search for the ideal thrombolytic agent. J. Am. Coll. Cardiol. 1987 November; 10(5 Suppl B):4B-10B.
22. Loscalzo J, Braunwald E. Tissue plasminogen activator. New England J. Med. 1988 October 6; 319(14):925-31.
23. Verstraete M, Collen D. Pharmacology of thrombolytic drugs. J. Am. College Cardiol. 1986 December; 8(6 Suppl B):33B-40B.
24. Hoyle, C E, Clark D. Polymer, 38, 5698 (1997).
25. Kaetsu, I Radiation synthesis of fabrications of biomedical applications, Radiat. Physics. Chem. 46 (4-6) 1995.
26. Tanaka, T. Phase transitions in gels and single polymers. Polymer 1979 20:1404-1412.
27. Patras G, Qiao G G, Solomon D H. Novel cross-linked homogeneous polyacrylamide gels with improved separation properties: Investigation of the cross-linker Functionality. Electrophoresis 2001, 22, 4303-4310.
28. Mandeville, III, et al., Ionic polymers as anti-infective agents U.S. Pat. No. 6,395,777 May 28, 2002.
29. Pharm. Res. 1989, volume 3, page 368. (See also 20.)
30. Vrachliotis T G, Rabkin D J, Berbaum K, Lang E V. Impact of unilateral common iliac vein occlusion on trapping efficacy of the Greenfield filter: an in vitro study. Acad. Radiol. 2001 June; 8(6):494-500.

What we claim is:

1. A medical device comprising:
a fiber support structure;
at least about 50 biocompatible fibers having a first end and a second end, wherein the first end of the fibers is constrained to the fiber support structure to form a bundle of non-woven fibers;
a wire connected to the fiber support structure to fix the first end of the fibers relative to the wire; and
a hypotube comprising a distal end, a proximal end and a central lumen wherein the wire extends through the central lumen of the hypotube,
wherein the bundle of non-woven fibers has a first configuration in which the fibers are confined within a narrow profile configuration and are all substantially aligned with each other and a second configuration in which the unconstrained portion of the fibers flares with respect to the narrow profile to form a porous filter matrix, wherein the flared fibers define a plurality of pores that are sized to trap emboli with sizes from about 50 microns to about 200 microns, wherein the relative position of the wire and the hypotube controls transition of the bundle of fibers between the first configuration and the second configuration, and wherein the bundle of fibers is a non-self extendable structure.

2. The medical device of claim 1 wherein the fibers comprise polymeric surface capillary fibers having surface capillaries that run substantially along the length of the fibers.

3. The medical device of claim 2 wherein the surface capillary fibers comprise polyester.

4. The medical device of claim 2 wherein the fibers have a specific capillary volume of at least about 0.5 cc/g.

5. The medical device of claim 1 wherein the fiber support structure comprises an adhesive that secures the fibers.

6. The medical device of claim 5 wherein the fibers are approximately coaxial within the secured adhesive.

7. The medical device of claim 1 wherein the hypotube has an outer diameter from about 0.04 inches to about 0.009 inches.

8. The medical device of claim 1 wherein the hypotube has an outer diameter of about 0.014 inches.

9. The medical device of claim 1 further comprising a catheter sheath over the hypotube that can selectively cover the fibers.

10. The medical device of claim 1 further comprising a treatment structure over the hypotube.

11. The medical device of claim 10 wherein the treatment structure comprises a balloon or a stent.

12. The medical device of claim 1 wherein the fiber support structure comprises a generally cylindrical polymer element.

13. The medical device of claim 1 wherein the fiber support structure comprises a band that encircles a bundle of fibers near the fiber ends to secure the fibers.

14. The medical device of claim 1 wherein the device in the first configuration can pass through a catheter with an appropriate size to enter a human vessel.

15. The medical device of claim 1 wherein the device in the second configuration has the center of the fibers flaring outward from the first end and the second end at a sufficient distance to fill the lumen of a human vessel.

16. The medical device of claim 1 wherein the device comprises from about 50 to about 5000 fibers.

17. The medical device of claim 1 wherein the device comprises fibers with a thickness from about 0.5 denier to about 25 denier.

18. The medical device of claim 1 wherein the bundle of fibers are twisted.

19. The medical device of claim 1 wherein both ends of the bundle of fibers are heat bonded.

20. A medical device comprising:
a plurality of biocompatible surface capillary fibers in a bundle,
a wire, and
a fiber support structure connected to the wire,
wherein at least one end of the surface capillary fibers is secured to the fiber support,
wherein the surface capillary fibers have a configuration to fill a lumen surrounding the attached end of the fiber with the lumen having a diameter corresponding to that of a human vessel with the fibers forming a porous filter matrix wherein the configuration of fibers defines a plurality of pores that are sized to allow the passage of a substantial majority of particulates that have a diameter less than 0.01 mm and trap emboli having a size larger than about 50 microns, and wherein each of the surface capillary fibers has a surface with at least one channel that extends substantially parallel to the length of the surface capillary fiber, the channel extending along at least a portion of the length of the surface capillary fiber and having a channel width from about 5 microns to about 250 microns.

21. The medical device of claim 20 wherein the surface capillary fiber has a thickness from about 0.5 deniers to about 50 deniers.

22. The medical device of claim 20 wherein the surface capillary fiber has a thickness from about 1 denier to about 20 deniers.

23. The medical device of claim 20 wherein the surface capillary fiber has a plurality of surface channels.

24. The medical device of claim 20 wherein the surface capillary fiber has a specific surface capillary volume of at least about 0.5 cc/g.

25. The medical device of claim 20 wherein the surface capillary fiber has a length from about 0.5 mm to about 25 mm.

26. The medical device of claim 20 further comprising additional fibers to have at least 25 fibers total.

27. The medical device of claim 20 further comprising additional fibers to have a total number from 50 fibers to 5000 fibers.

28. The medical device of claim 20 wherein the fiber support structure comprises a first element and a second element wherein the bundle of fibers is attached at one end to the first element and at a second end to the second element.

29. The medical device of claim 28 wherein the first element has a generally cylindrical shape and a central lumen.

30. The medical device of claim 29 further comprising a plurality of additional surface capillary fibers wherein each fiber is attached at a first end to the first element and at a second end to the second element and wherein the wire passes through the central lumen of the first element and attaches to the second element.

31. The medical device of claim 30 wherein the surface capillary fibers are attached to the first element and the second element with an orientation in which the support structure has a first configuration with the first element and the second element separated appropriate to have the surface capillary fibers in a generally straight position between the elements to form a bundle with a generally cylindrical orientation and a second configuration with the ends of the fibers pulled generally toward each other and the centers of the fibers bulging outwardly from the generally cylindrical orientation.

32. The medical device of claim 20 wherein the fiber support structure comprises an adhesive.

33. An embolism entrapment system comprising a hypotube having a central lumen, medical device of claim 20 wherein the wire has a diameter appropriate to pass through the central lumen of the hypotube, and a treatment structure suitable for delivery over the hypotube.

34. The embolism entrapment system of claim 33 wherein the treatment structure comprises a balloon or a stent.

35. The embolism entrapment system of claim 33 further comprising a catheter sheath with an inner diameter suitable for removable placement of the catheter sheath over the hypotube to cover the surface capillary fibers.

36. A medical device comprising:
a hypotube having a distal end, a proximal end, and a central channel lumen,
a wire having a distal end and a proximal end,
a coil, and
a filter device comprising a bundle of polymer fibers having a first end and a second end,
wherein the fibers are operably constrained at the first end to the distal end or near the distal end of the hypotube at a first attachment point and operably constrained at the second end to the distal end or near the distal end of the wire at a second attachment point, such that the fiber bundle has a first low profile configuration wherein all of the fibers in the bundle are substantially aligned with each other and a second configuration with the unconstrained portion of the fibers flaring into a non-woven porous filter matrix, wherein the flared fibers define a plurality of pores that are sized to trap emboli with sizes from about 50 microns to about 200 microns,
wherein the bundle of fibers is a non-self extendable structure,
wherein the wire extends through the central lumen of the hypotube in a distal direction beyond the first and second attachment points, and
wherein the coil is located over the distal end of wire distal to the second attachment point.

37. The medical device of claim 36 wherein the first low profile configuration is a delivery configuration for deployment and the second configuration is a deployed configuration.

38. The medical device of claim 36 wherein the hypotube has a diameter no more than about 0.040 inches.

39. The medical device of claim 36 wherein the fibers have a length from about 0.5 mm to about 25 mm.

40. The medical device of claim 36 wherein the hypotube has a diameter of about 0.014 inches.

41. The medical device of claim 36 wherein the distal end of the hypotube is tapered.

42. The medical device of claim 36 wherein the distal end of the hypotube comprises a metal coil.

43. The medical device of claim 36 wherein the wire has a diameter of from about 0.003 to about 0.008 inches.

44. The medical device of claim 36 wherein the fibers are surface capillary fibers having surface capillaries that run substantially along the length of the fibers.

45. The medical device of claim 36 wherein the bundle of polymer fibers comprises at least 50 fibers.

46. The medical device of claim 36 wherein movement of the wire relative to the hypotube changes the configuration of the filter device.

47. The medical device of claim 46 wherein translating the distal end of the wire toward the distal end of the hypotube brings the ends of the fibers closer together to force the center of the fibers away from a central axis along the hypotube to form the non-woven porous filter matrix.

* * * * *